(12) United States Patent
Prasad et al.

(10) Patent No.: US 7,479,540 B1
(45) Date of Patent: Jan. 20, 2009

(54) ADIPOMODULIN AND RELATED MOLECULES AND METHODS

(76) Inventors: Chandan Prasad, 69 Marywood Ct., New Orleans, LA (US) 70101; Julio E. Figueroa, II, 86 Oriole St., New Orleans, LA (US) 70101; Parakat Vijayagopal, 57 Brittany Dr., Kenner, LA (US) 70062

( * ) Notice: Subject to any disclaimer, the term of this patent is extended or adjusted under 35 U.S.C. 154(b) by 385 days.

(21) Appl. No.: 11/099,329

(22) Filed: Apr. 5, 2005

Related U.S. Application Data

(62) Division of application No. 10/744,535, filed on Dec. 22, 2003, now abandoned.

(51) Int. Cl.
*C07K 14/00* (2006.01)
(52) U.S. Cl. .................... 530/350; 530/387.1; 530/412; 530/828; 530/829; 530/868
(58) Field of Classification Search ........................ None
See application file for complete search history.

(56) References Cited

U.S. PATENT DOCUMENTS

| | | | |
|---|---|---|---|
| 4,871,663 | A | 10/1989 | Oshima et al. |
| 6,274,550 | B1 | 8/2001 | Prasad et al. |

FOREIGN PATENT DOCUMENTS

WO    WO 88/00206    1/1998

OTHER PUBLICATIONS

Anonymous, "Overweight, Obesity, and Health Risk," Archives of Internal Medicine, vol. 160, pp. 898-904 (2000).
Bjorntorp, P., "Adipose tissue distribution and function," Int. Journal Obesity, vol. 2 (15 Suppl.), pp. 67-81 (1991).
Boehm, B. O., "The therapeutic potential of somatostatin receptor ligands in the treatment of obesity and diabetes," Expert Opin. Investig. Drugs, (9):1501-9 (Sep. 9, 2003).
Bradley, D. C. & Kaslow, H. R., "Radiometric assays for glycerol, glucose and glycogen," Anal. Biochem. vol. 180, pp. 11-16 (1989).
Brasaemle in Brasaemle, D. L., Levin, D. M., Adler-Wailes, D. C., & Londos, C., "The lipolytic stimulation of 3T3-L1 adipocytes promotes the translocation of hormone-sensitive lipase to the surfaces of lipid storage droplets," Bioch. Biophys. Acta., 1483(2):251-262 (Jan. 17, 2000).
Bray, G. A. & Tartaglia, L. A., "Medicinal strategies in the treatment of obesity," Nature, vol. 404, pp. 672-677 (2000).
Carek, P. J. & Dickerson, L. M., "Current concepts in the pharmacological management of obesity," Drugs, vol. 57, pp. 883-904 (1999).
Chance, R. E., & Frank, B. H., "Research, development, production, and safety of biosynthetic human insulin," Diabetes Care, 16 Suppl 3:133-42 (1993).
Chyung, Y. H., Peng, P. D., & Kay, M. A., "System for simultaneous tissue-specific and disease-specific regulation of therapeutic gene expression," Hum. Gene Ther., 14(13):1255-64 (Sep. 1, 2003).
Cowherd, R. M., Lyle, R. E. & McGehee, R. E., Jr., "Molecular regulation of adipocyte differentiation," Seminars in Cell & Dev. Biol., vol. 10, pp. 3-10 (1999).

De Brabander, C., Vervaet, C., & Remon, J. P., "Development and evaluation of sustained release mini-matrices prepared via hot melt extrusion," J. Control Release, 89(2):235-47 (Apr. 29, 2003).
Ed Harlow & David Lane, "Antibodies. A Laboratory Manual," pp. 471-510, Cold Spring Harbor Laboratory, Cold Spring Harbor, New York (1988).
Figueroa, J.E., Vijayagopal, P, Prasad, A., Schapira, D.V. and Prasad, C., "Isolation, characterization, and distribution of a 24-kDa proteoglycan in the urine of cachectic cancer and AIDS patients." Biochem. Biophys. Res. Commun. 254:642-46 (1999).
Figueroa, J.E., Vijayagopal, P., & Prasad, C. 2002. Azaftig stimulates in vitro lipolysis by rodent and human adipocytes. Biochemical and Biophysical Research Communications. 293:847-49.
Figueroa, J.E., Vijayagopal, P., Debata, C., Prasad, A. & Prasad, C. , "Azaftig, a urinary proteoglycan from a cachectic cancer patient, causes profound weight loss in mice." Life Sci. 64:1339-1347 (1999).
Fischer, P. M., "The Design, Synthesis and Application of Stereochemical and Directional Peptide Isomers: A Critical Review," Curr. Protein Pept. Sci., (5):339-356 (Oct. 4, 2003).
Fontaine, K. R., Redden, D. T., Wang, C., Westfall, A. O., & Allison, D. B., "Years of life lost due to obesity," JAMA, vol. 28, pp. 187-193 (2003).
Fujioka S., Matsuzawa Y., Tokunaga K., Kawamoto T., Kobatake T., Keno Y., Kotani K., Yoshida S. & Tarui S., "Improvement of glucose and lipid metabolism associated with selective reduction of intra-abdominal visceral fat in premenopausal women with visceral fat obesity," Int. Journal Obesity, vol. 15, pp. 853-859 (1991).
Greenberg, A. S., Shen, W., Muliro, K., Patel, S., Souza, S. C., Roth, R. A., & Kraemer, F. B., "Stimulation of Lipolysis and Hormone-sensitive Lipase via the Extracellular Signal-regulated Kinase Pathway," J. Biol. Chem., 276: 45456-45461 (2001).
Greenwood, F. C., Hunter, W. L., & Glover J. J., "The preparation of 131I labeled growth hormone of high specific activity," Biochem. J., vol. 89, pp. 114-123 (1963).
Haemmerle, G., Zimmermann, R., Hayn, M., Theussl, C., Waeg, G., Wagner, E., Sattler, W., Magin, T. M., Wagner, E. F., & Zechner, R., "Hormone-sensitive lipase deficiency in mice causes diglyceride accumulation in adipose tissue, muscle, and testis," J. Biol. Chem., 277(7):4806-15 (Feb. 15, 2002).
Hakansson, S., Viljanen, J., & Broo, K. S., "Programmed delivery of novel functional groups to the alpha class glutathione transferases," Biochemistry, 42(34):10260-8 (Sep. 2, 2003).
Heinrikson, R.L., "The Edman degradation in protein sequence analysis" in Biochemical and Biophysical Studies of Proteins and Nucleic Acids, T-B Lo et al., Eds. (Elsevier, New York, 1984), pp. 285-302.
Heller, S., "Insulin lispro: a useful advance in insulin therapy," Expert Opin. Pharmacother., (8):1407-1 (Aug. 4, 2003).

(Continued)

*Primary Examiner*—Manjunath Rao
*Assistant Examiner*—Daniel C Gamett
(74) *Attorney, Agent, or Firm*—Jason P. Mueller; Adams and Reese LLP

(57) ABSTRACT

Adipomodulin (a light chain molecule) and related molecules and methods useful in the treatment of obesity and obesity-related disorders.

5 Claims, 13 Drawing Sheets

OTHER PUBLICATIONS

Hirsch, A. H. & Rosen, O. M., "Lipolytic stimulation modulates the subcellular distribution of hormone-sensitive lipase in 3T3-L1 cells," J. Lipid Res., vol. 25, pp. 665-667 (1984).

Holm, C., Østerlund, T., Laurell, H., & Contreras, J. A., "Molecular mechanisms regulating hormone sensitive lipase and lipolysis." Annu. Rev. Nutr., 20:365-93 (2000).

Jatinderpal Kalsi, Chelliah T. Ravirajan, Anisur Rahman, & David A. Isenberg, "Structure-function analysis and the molecular origins of anti-DNA antibodies in systemic lupus erythematosus," Exp. Rev. Mol. Med. Feb. 16, 1999, http://www-ermm.cbcu.cam.ac.uk/99000423h.htm.

Katayama, K., Kato, Y., Onishi, H., Nagai, T., & Machida, Y., "Double liposomes: hypoglycemic effects of liposomal insulin on normal rats," Drug Dev. Ind. Pharm., (7)7 (Aug. 29, 2003).

Kotenko, S. V., Izotova, L. S., Mirochnitchenko, O. V., Esterova, E., Dickensheets, H., Donnelly, R. P., & Pestka, S., "Identification, cloning, and characterization of a novel soluble receptor that binds IL-22 and neutralizes its activity," J. Immunol., 166(12):7096-103 (Jun. 15, 2001).

Lafontan, M. & Berlan M., "Do regional differences in adipocyte biology provide new pathophysiological insights?" Trends in Pharmacological Sciences, vol. 24, Issue 6, pp. 276-283 (2003).

Langin, D., Lucas, S. & Lafontan, M., "Millennium fat-cell lipolysis reveals unsuspected novel tracks," Hormone & Metab. Res., vol. 32, pp. 443-452 (2000).

Lim, A., Wally, J., Walsh, M. T., Skinner, M., & Costello, C. E., "Identification and location of a cysteinyl posttranslational modification in an amyloidogenic kappa1 light chain protein by electrospray ionization and matrix-assisted laser desorption/ionization mass spectrometry," Anal. Biochem., 295(1):45-5 (Aug. 1, 2001).

Mauriege, P., Imbeault, P., Langin, D., Lacaille, M., Almeras, N., Tremblay, A. & Despres, J. P., "Regional and gender variations in adipose tissue lipolysis in response to weight loss," J. Lipid Res., vol. 40, pp. 1559-1571 (1999).

McCarthy, W. J., Arpawong, T. E., Dietsch, B. J., & Yancey, A. K., "Effects of exercise and weight loss on hypertension," JAMA, vol. 290, pp. 885-886 (2003).

Mehdi, S. Q. & Nussey, S. S., "A radio-ligand receptor assay for the long-acting thyroid stimulator," Biochem. J. 145:105-111 (1975).

Osuga, J., Ishibashi, S., Oka, T., Yagyu, H., Tozawa, R., Fujimoto, A., Shionoiri, F., Yahagi, N., Kraemer, F. B., Tsutsumi, O., & Yamada, N., "Targeted disruption of hormone-sensitive lipase results in male sterility and adipocyte hypertrophy, but not in obesity," Proc. Natl. Acad. Sci. USA., 97(2):787-92 (Jan. 18, 2000).

Pi-Sunyer, F. X., "Comorbidities of overweight and obesity: current evidence and research issues," Medicine & Science in Sports & Exercise, vol. 31 (11 Suppl.), pp. S602-S608 (1999).

Prins, J. B, Walker, N. I., Winterford, C. M. & Cameron, D. P., "Human adipocyte apoptosis occurs in malignancy.," Biochem. Biophys. Res. Commun., vol. 205, pp. 625-630 (1994).

Rangwala, S. M. & Lazar, M. A., "Transciptional control of adipogenesis," Ann. Rev. Nutrition., vol. 20, pp. 535-559 (2000).

Rapoport, B., Chazenbalk, G. D., Jaume, J. C., & McLachlan, S. M., "The thyrotropin (TSH) receptor: interaction with TSH and autoantibodies," Endocr. Rev., 19: 673-716 (1997).

Redmon, J. B., Raatz, S. K., Reck, K. P., Swanson, J. E., Kwong, C. A., Fan, Q., Thomas, W., & Bantle, J.P., "One-year outcome of a combination of weight loss therapies for subjects with type 2 diabetes: a randomized trial," Diabetes Care, vol. 26, pp. 2505-2511 (2003).

Rees, Smith B., & Hall, R., "Thyroid-stimulating immunoglobulins in Graves' disease," Lancet 2:427-431 (1974).

Robbins, P. D. & Ghivizzani, S. C., "Viral vectors for gene therapy," Pharmacol. Ther., 80(1):35-47 (Oct. 1998).

Rodbell, M., Metabolism of isolated fat cells, J. Biol. Chem., 239: 375-380 (1964).

Rosen, E. D., Walkey, C. J., Puigserver, P. & Spiegelman, B. M., "Transcriptional regulation of adipogenesis. Genes & Development," vol. 14, pp. 1293-1307 (2000).

Sengenes, C., Berlan, M., De Glisezinski, I., Lafontan, M., & Galitzky, J., "Natriuretic peptides: a new lipolytic pathway in human adipocytes," FASEB J., 14(10):1345-51 (Jul. 2000).

Sengenes, C., Zakaroff-Girard, A., Moulin, A., Berlan, M., Bouloumie, A., Lafontan, M., & Galitzky, J., "Natriuretic peptide-dependent lipolysis in fat cells is a primate specificity," Am. J. Physiol. Regul. Integr. Comp. Physiol., 283(1):R257-65 (Jul. 2002).

Sethi, J. K. & Hotamisligil, G. S., "The role of TNF alpha in adipocyte metabolism," Seminars in Cell & Dev. Biol., vol. 10, pp. 19-29 (1999).

Shi, H., Norman, A. W., Okamura W. H. & Zemel, M. B., "1alpha,25-dihyroxyvitamin D3 modulates human adipocyte metabolism via nongenomic action," FASEB J. 15, 2751-2753 (2001).

Shi, H., Norman, A. W., Okamura, W. H., Sen, A., & Zemel, M. B., "1alpha,25-Dihydroxyvitamin D3 modulates human adipocyte metabolism via nongenomic action," FASEB J. 15:2751-2753 (2001).

Siegel, D. L., "Selecting antibodies to cell-surface antigens using magnetic sorting techniques," Methods Mol. Biol., 178:219-26 (2002).

Sorisky A., Magun R. & Gagnon, A. M., "Adipose cell apoptosis: death in the energy depot," Int. J. Obesity & Related Metab. Disorders, vol. 4 (24 Suppl.), pp. S3-S7 (2000).

Spiegelman, B. M., Puigserver, P. & Wu, Z., "Regulation of adipogenesis and energy balance by PRARgamma and PGC-1," Int. J. Obesity & Rel. Metab. Dis., vol. 4 (24 Suppl.), pp. S8-S10 (2000).

Srour, M. A., Fechner, H., Wang, X., Siemetzki, U., Albert, T., Oldenburg, J., Hanfland, P., Poller, W., Brackmann, H. H., & Schwaab, R., "Regulation of human factor IX expression using doxycycline-inducible gene expression system," Thromb. Haemost., 90(3):398-40 (Sep. 2003).

Stewart et al., "Solid-Phase Peptide Synthesis," W. H. Freeman Co., San Francisco, Calif. (1969); Merrifield, J., Am. Chem. Soc., 85:2149-2154 (1963).

The Look AHEAD Research Group, "Look AHEAD (Action for Health in Diabetes): design and methods for a clinical trial of weight loss for the prevention of cardiovascular disease in type" 2 diabetes, Control Clin. Trials, vol. 24, pp. 610-628 (2003).

van Deutekom, J. C. & van Ommen, G. J., "Advances in Duchenne muscular dystrophy gene therapy," Nat. Rev. Genet., 4(10):774-83 (Oct. 2003).

Vahle, J. L., Sato, M., Long, G. G., Young, J. K., Francis, P. C., Engelhardt, J. A., Westmore, M. S., Linda, Y., & Nold, J. B., "Skeletal changes in rats given daily subcutaneous injections of recombinant human parathyroid hormone (1-34) for 2 years and relevance to human safety," Toxicologic Pathology, 30(3):312-21 (2002).

Van, R. L. & Roncari, D. A., "Complete differentiation of adipocyte precursors. A culture system for studying the cellular nature of adipose tissue.," Cell & Tissue Res., vol. 195, pp. 317-329 (1978).

Vernon, R. G., Barber, M. C. & Travers, M. T. "Present and future studies on lipogenesis in animals and human subjects," Proc. Nutrition Soc., vol. 58, pp. 541-549 (1999).

Wang, S. P., Laurin, N., Himms-Hagen, J., Rudnicki, M.A., Levy, E., Robert, M. F., Pan, L., Oligny, L., & Mitchell, G. A., "The adipose tissue phenotype of hormone-sensitive lipase deficiency in mice," Obes. Res., 9(2):119-28 (Feb. 2001).

William Paul, Fundamental Immunology, Fifth Edition, chapters 3, 4, and 5 (2003).

Xiao, Q., Jeng, W., & Wheeler, M. B., Characterization of glucagon-like peptide-1 receptor-binding determinants, J. Mol. Endocrinol., 25(3):321-35) (Dec. 2000).

Zheng, Y., Rozengurt, N., Ryazantsev, S., Kohn, D. B., Satake, N., & Neufeld, E. F., "Treatment of the mouse model of mucopolysaccharidosis I with retrovirally transduced bone marrow," Mol. Genet. Metab. 79(4):233-44 (Aug. 2003).

Zhou, Y. T., Wang, Z. W., Higa, M., Newgard, C.B. & Unger, R. H., "Reversing adipocyte differentiation: implications for treatment of obesity," Proc. Nat. Acad. Sci. of the U.S.A., vol. 96, pp. 2391-2395 (1999).

Geysen et al. The Journal of Molecular Recognition (1998), vol. 1(1): pp. 32-41, esp. p. 39: paragraph 3, lines 1-3.

Path et al., The Journal of Endocrinology & Metabolism (2001), vol. 86 (5): pp. 2281-2288, esp. p. 2287: col. 1, lines 1-12.

Okazaki et al., Diabetes (2001), vol. 51: pp. 3368-337.5, esp. p. 3369: col. 1, lines 5-12.

PRIMARY STRUCTURE OF KAPPA LIGHT CHAIN

| | | | |
|---|---|---|---|
| DIQMTQSPDS<br>1 | LAVSLGERAT<br>11 | VNCKSSQSIL<br>21 | YSSNSKNYLA<br>31 |
| WYQQKPGQPP<br>41 | TLLIYWASTR<br>51 | QSGVPDRFSG<br>61 | SGSGTNFTLT<br>71 |
| ISNLQTEDVA<br>81 | VYYCQQYYTA<br>91 | PFTFGPGTTV<br>101 | HIKRTVAAPS<br>111 |
| VFIFPPSDEQ<br>121 | LKSGTASVVC<br>131 | LLNNFYPREA<br>141 | KVQWKVDNAL<br>151 |
| QSGNSQESVT<br>161 | EQDSKDSTYS<br>171 | LSSTLTLSKA<br>181 | DYEKHKVYAC<br>191 |
| EVTHQGLSSP<br>201 | VTKSFNRGEC<br>211 | | |

FIG. 2

COMPARISON OF PHYSICAL AND CHEMICAL PROPERTIES OF AZAFTIG AND ADIPOMODULIN

| Characteristics | $^{125}$I-Azaftig (Original patent) | $^{25}$I-Preparation 116 | $^{25}$I-Preparation 121 | $^{25}$I-Preparation 122 | $^{25}$I-Preparation 212 |
|---|---|---|---|---|---|
| Binding to fat cells | yes | Not done | Not done | yes | Not done |
| Stimulation of lipolysis | yes | yes | yes | yes | yes |
| Molecular size (approximate) | 24KDa | 25-30KDa | 25-30KDa | 25-30KDa | 25-30KDa |
| Related to light chain | yes | yes | yes | yes | yes |
| Digestion by neuraminidase | no | no | no | no | no |
| Digestion by chondroitinase AC | yes | no | no | no | no |
| Digestion by chondroitinase ABC | yes | no | no | no | no |
| Chemical nature | Chondroitin.SO$_4$.Dermatan.SO$_4$ containing proteoglycan | Not a proteoglycan | Not a proteoglycan | Not a proteoglycan | Not a proteoglycan |

FIG. 4

THE L CHAIN MOLECULE

```
                        SEQUENCE LISTING

<160> NUMBER OF SEQ ID NOS: 3

<210> SEQ ID NO 1
<211> LENGTH: 10
<212> TYPE: PRT
<213> ORGANISM: Homo sapiens

<400> SEQUENCE: 1

Asp Ile Gln Met Thr Gln Ser Pro Ser Ser
1               5                   10

<210> SEQ ID NO 2
<211> LENGTH: 10
<212> TYPE: PRT
<213> ORGANISM: Homo sapiens

<400> SEQUENCE: 2

Glu Ile Val Leu Thr Gln Ser Pro Gly Thr
1               5                   10

<210> SEQ ID NO 3
<211> LENGTH: 220
<212> TYPE: PRT
<213> ORGANISM: Homo sapiens

<400> SEQUENCE: 3

Asp Ile Gln Met Thr Gln Ser Pro Asp Ser Leu Ala Val Ser Leu Gly
```

-continued

```
1               5                    10                   15
Glu Arg Ala Thr Val Asn Cys Lys Ser Ser Gln Ser Ile Leu Tyr Ser
            20                  25                  30

Ser Asn Ser Lys Asn Tyr Leu Ala Trp Tyr Gln Gln Lys Pro Gly Gln
            35                  40                  45

Pro Pro Thr Leu Leu Ile Tyr Trp Ala Ser Thr Arg Gln Ser Gly Val
            50                  55                  60

Pro Asp Arg Phe Ser Gly Ser Gly Ser Gly Thr Asn Phe Thr Leu Thr
65                      70                  75                  80

Ile Ser Asn Leu Gln Thr Glu Asp Val Ala Val Tyr Tyr Cys Gln Gln
                85                  90                  95

Tyr Tyr Thr Ala Pro Phe Thr Phe Gly Pro Gly Thr Thr Val His Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220
```

ADIPOMODULIN AND RELATED MOLECULES AND METHODS

This application is a divisional of application Ser. No. 10/744,535, filed Dec. 22, 2003, which is hereby incorporated herein by reference in its entirety.

In certain embodiments presented herein, the present invention relates to molecules which bind to fat cells to promote lipolysis. Other embodiments relate to light chain molecules and light chain molecule variants and fragments, as well as agents that mimic these, which bind to fat cells to promote lipolysis. Also presented are embodiments of the present invention that relate to the use of these molecules in the treatment of obesity and obesity-related disorders.

I. BRIEF DESCRIPTION OF THE SEVERAL VIEWS OF THE DRAWINGS

FIG. 2 is an amino acid sequence listing of the generic light chain [SEQ ID NO: 3].

FIG. 4 is a comparison chart of the physical and chemical properties of azaftig and adipomodulin.

Figure 1:
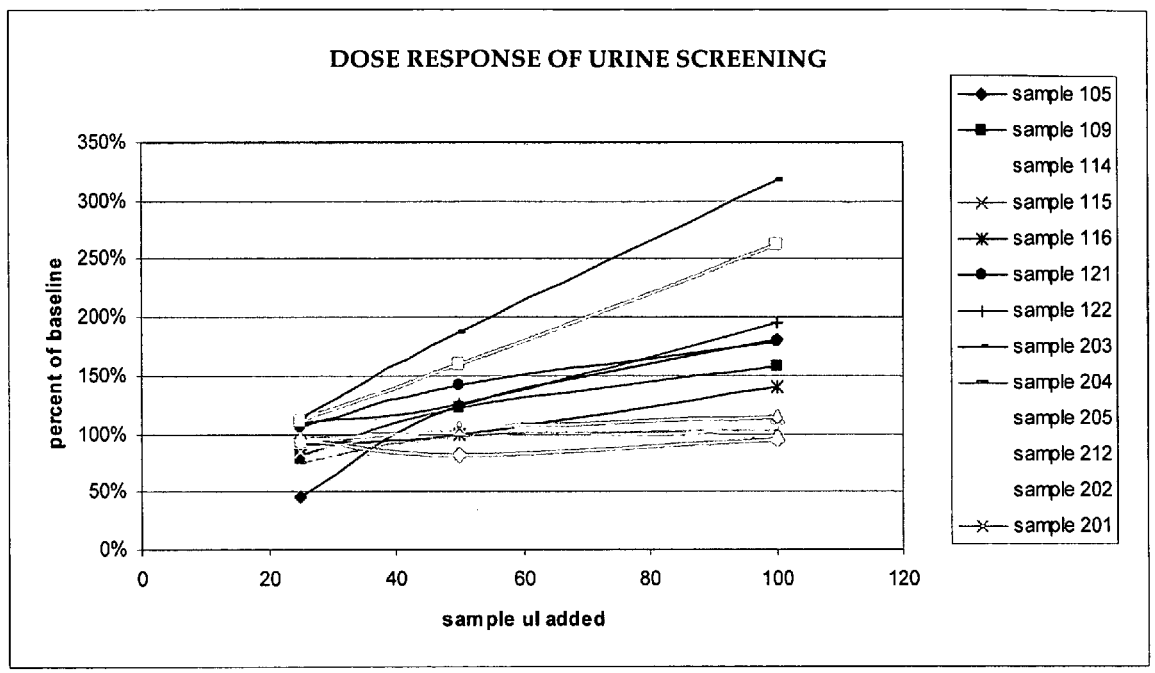
FIG. 1 is a graph of results of screening urine for lipolysis enhancement. The data are presented as percentage of change in basal glycerol release (an index of lipolysis).

FIG. 9 contains the models of lipolysis outlined in the text. Panel (a) shows the classical model; panel (b) shows the cGMP model; panel (c) shows the PKC model; panel (d) shows the Calcium model; and panel (e) shows the lipase model involving adipomodulin.

II. DETAILED DESCRIPTION OF THE INVENTION

Obesity is an increase in body weight beyond the limitation of the body's requirements, as the result of an excessive accumulation of fat. A person is considered to be overweight if he or she has a body mass index of 25 to 30, and a person is considered to be obese if he or she has a body mass index of greater than 30. Body mass index is a calculation of weight divided by height. The calculation gives a sense of the amount of fat a person has in his or her body.

The population of the United States is the most obese population in the world. More than 50% of the adult population is overweight, and 20% is considered obese. Being overweight or obese increases the risks for hypertension, coronary heart disease, stroke, diabetes, gallbladder diseases, degenerative joint disease, sleep apnea, and certain cancers. Obesity is the second highest cause of preventable death in the United States (exceeded only by cigarette smoking); it is estimated to affect 58,000,000 people and contribute to 300,000 deaths annually. The effects of obesity appear to be most acute in the younger populations (Fontaine, K. R., Redden, D. T., Wang, C., Westfall, A. O., & Allison, D. B., "Years of life lost due to obesity," JAMA, vol. 28, pp. 187-193 (2003), which is incorporated herein by reference in its entirety). For example, young white men with morbid obesity have a 12-year shorter life span than those with normal body weight (ibid.). Because of the tremendous health implications associated with being overweight or obese, the Centers for Disease Control and Prevention has identified a number of obesity-related conditions as priority areas for "Healthy People 2010," its comprehensive, nationwide health promotion and disease prevention agenda.

The United States government estimates that $100 billion is spent every year to treat obesity. Current treatments include the following, alone or in combination: diet, exercise, behavior modification, surgical intervention, and pharmacological intervention. While the combination of diet and exercise is the safest treatment, it requires a great deal of discipline and, therefore, has not been very popular. Surgical intervention has been shown to be relatively effective, but it is advised only for morbidly obese people and involves a number of complications. There is a great deal of work being done in the area of pharmacological treatments for obesity.

Obesity is generally classified into two groups based on the site of fat deposition—visceral and nonvisceral, also known as upper-body/android (apple-shaped) and lower-body/gynoid (pear-shaped) obesity, respectively. It is well established that visceral adipose tissue is associated with greater morbidity and mortality, particularly hypertension, hyperlipidemia, and insulin resistance (Pi-Sunyer, F. X., "Comorbidities of overweight and obesity: current evidence and research issues," Medicine & Science in Sports & Exercise, vol. 31 (11 Suppl.), pp. S602-8 (1999), which is incorporated herein by reference in its entirety). Data show that weight loss by diet, exercise, or pharmacotherapy generates a decrease in visceral adipose tissue and improvements in hypertension, hyperlipidemia, and insulin resistance (Bray, G. A. & Tartaglia, L. A., "Medicinal strategies in the treatment of obesity," Nature, vol. 404, pp. 672-677 (2000), which is incorporated herein by reference in its entirety.)

There are currently a number of strategies for drug development for the treatment of obesity: (1) reducing food intake either by amplifying inhibitory effects of anorexigenic signals or factors (those that suppress food intake) or by blocking orexigenic signals or factors (those that stimulate food intake); (2) blocking nutrient absorption (especially fat) in the gut; (3) increasing thermogenesis (the physiologic process of heat production in the body) by uncoupling of fuel metabolism from the generation of adenosine triphosphate (ATP), thereby dissipating food energy as heat; (4) modulating fat metabolism or storage by regulating fat synthesis (lipogenesis), fat breakdown (lipolysis), adipose differentiation (adipogenesis), and/or fat cell death (apoptosis); and (5) modulating the central controller regulating body weight by altering the internal reference value sought by the controller, or by modulating the primary afferent signals regarding fat stores that are analyzed by the controller. This approach would have the potential advantage of forcing the endogenous controller to regulate multiple pathways of energy balance and minimize compensation (Bray & Tartaglia, 2000).

In many respects, obesity is analogous to hypertension, a chronic disease modulated by several levels of feedback regulation. Several generations of anti-hypertensive drugs have shaped our understanding of the blood pressure feedback system. A similar situation is predicted for anti-obesity medications. Like hypertension, it is reasonable to expect that for many obese patients, effective therapy will involve chronic use of more than one drug. However, our experiences with many drugs aimed at reducing food intake have not been very rewarding due to serious side effects. Thus, any approved drug will be required to meet high standards of safety.

Currently, there is no available pharmacotherapy that facilitates a decrease in fat deposit. Anorectic centrally acting agents such as fenfluoramine, phentermine, dexfenfluramine and sibutramine have been successful in obesity treatment; however, some of these agents have been removed from the market due to serious side effects (Bray & Tartaglia, 2000). Orlistat, an intestinal lipase inhibitor, has been shown to cause weight loss in subjects who tolerate a low fat diet, but the drug causes gastrointestinal side effects (ibid.). A pharmacological treatment that reduces body fat, while avoiding serious side effects would be of great health significance.

At any given time, adipose tissue mass reflects the number and average volume of adipocytes (animal connective tissue cells specialized for the synthesis and storage of fat), both of these parameters being under complex control. The major contributor to adipocyte volume is cytoplasmic triglyceride, which is determined by the balance between lipogenesis (the production of fat cells) and lipolysis (the breakdown of fat cells). Both lipogenesis and lipolysis have a number of positive and negative regulators (see Table 1 below). Adipocyte number, on the other hand, is determined by the relative rate of cell acquisition by preadipocyte replication/differentiation. Preadipocytes are precursor cells from which adipocytes are derived. Preadipocytes multiply. These cells also differentiate into mature adipocytes after undergoing signaling that appears to involve certain nuclear binding proteins (e.g., peroxisome proliferator activated-receptor (PPAR) gene productions). Mature adipocytes are terminally differentiated and, therefore, do not multiply (see Van, R. L. & Roncari, D. A., "Complete differentiation of adipocyte precursors. A culture system for studying the cellular nature of adipose tissue.," Cell & Tissue Res., vol. 195, pp. 317-29 (1978), which is incorporated herein by reference in its entirety). Adipocyte number is also determined by the rates of cell loss by apoptosis (the programmed destruction of cells from within) (see Prins, J. B, Walker, N. I., Winterford, C. M. & Cameron, D. P., "Human adipocyte apoptosis occurs in malignancy.," Biochem. Biophys. Res. Commun., vol. 205, pp. 625-30 (1994), which is incorporated herein by reference in its entirety) and dedifferentiation of adipocytes. Dedifferentiation is a novel concept. Generally, the idea is that high expression of certain molecules (for instance, leptin) can cause the return of differentiated adipocyte cells into preadipcytes. This leads to loss of mature adipocytes and, therefore, fat (see Zhou, Y. T., Wang, Z. W., Higa, M., Newgard, C. B. & Unger, R. H., "Reversing adipocyte differentiation: implications for treatment of obesity," Proc. Nat. Acad. Sci. of the U.S.A., vol. 96, pp. 2391-5 (1999)), which is incorporated herein by reference in its entirety). A change in adipose tissue mass must involve a change in adipocyte number, adipocyte volume, or both. It has been shown that a reduction in adipocyte volume and number occurs in loss of adipose tissue (Mauriege, P., Imbeault, P., Langin, D., Lacaille, M., Almeras, N., Tremblay, A. & Despres, J. P., "Regional and gender variations in adipose tissue lipolysis in response to weight loss," J. Lipid Res., vol. 40, pp. 1559-71 (1999), which is incorporated herein by reference in its entirety). Indeed, current evidence suggests that a significant increase or decrease in fat mass involves a change in both parameters. It has also been observed that during weight gain, adipocyte volume increases to a "critical" point, after which recruitment of new cells occurs (Bjorntorp, P., "Adipose tissue distribution and function," Int. Journal Obesity, vol. 2 (15 Suppl.), pp. 67-81 (1991), which is incorporated herein by reference in its entirety). As noted, Table 1 illustrates the modulators of the fat depot:

TABLE 1

| Modulators | Increase | Decrease |
|---|---|---|
| Fat Cell Volume | | |
| 1. Lipogenesis | Insulin, EGF, Angiotensin II, glucocorticoids | GH, TNF-α |
| 2. Lipolysis | GIP, GH, Leptin, TNF-α, NPY-antagonist | Insulin, NPY |
| Fat Cell Number | | |
| 1. Differentiation of preadipocytes to adipocytes | Insulin, glucocorticoids | EGF, TNF-α |
| 2. Dedifferentiation of adipocytes to preadipocytes | Leptin | |
| 3. Apoptosis of: | | |
| (a) adipocytes | Leptin, TNF-α, NPY-antagonist | NFκB, bcl-2, Insulin |
| (b) preadipocytes | Retinoic acid, leptin, TNF-α | |

(see Cowherd, R. M., Lyle, R. E. & McGehee, R. E., Jr., "Molecular regulation of adipocyte differentiation," Seminars in Cell & Dev. Biol., vol. 10, pp. 3-10 (1999); Langin, D., Lucas, S. & Lafontan, M., "Millennium fat-cell lipolysis reveals unsuspected novel tracks," Hormone & Metab. Res., vol. 32, pp. 443-52 (2000); Rangwala, S. M. & Lazar, M. A., "Transcriptional control of adipogenesis," Ann. Rev. Nutrition., vol. 20, pp. 535-59 (2000); Rosen, E. D., Walkey, C. J., Puigserver, P. & Spiegelman, B. M., "Transcriptional regulation of adipogenesis. Genes & Development," vol. 14, pp. 1293-1307 (2000); Sethi, J. K. & Hotamisligil, G. S., "The role of TNF alpha in adipocyte metabolism," Seminars in Cell & Dev. Biol., vol. 10, pp. 19-29 (1999); Sorisky A., Magun R. & Gagnon, A. M., "Adipose cell apoptosis: death in the energy depot," Int. J. Obesity & Related Metab. Disorders, vol. 4 (24 Suppl.), pp. S3-7 (2000); Spiegelman, B. M., Puigserver, P. & Wu, Z., "Regulation of adipogenesis and energy balance by PPARgamma and PGC-1," Int. J. Obesity & Rel. Metab. Dis., vol. 4 (24 Suppl.), pp. S8-10 (2000); Vernon, R. G., Barber, M. C. & Travers, M. T. "Present and future studies on lipogenesis in animals and human subjects," Proc. Nutrition Soc., vol. 58, pp. 541-9 (1999), all of which are incorporated herein by reference in their entireties).

An effective strategy for controlling obesity will involve the development of substances that modulate one or more aspects of fat metabolism and storage, resulting in diminution of the fat depot. Substances that deplete the fat depot are more desirable than substances directed to curb appetite or desire to eat for many reasons. First, substances known to decrease food intake or desire to eat are generally known to act at the level of the central nervous system and involve one or more of the ever present neurotransmitters (e.g., norepinephrine, serotonin, and dopamine). These neurotransmitters are also ubiquitously distributed throughout the central nervous system. They are associated with a variety of other functions in addition to food intake, and modulators of these neurotransmitters are not exclusively specific to food intake signals. The side effects associated with these neurotransmitters stem from these other effects on central function. Therefore, substances that act at the level of the central nervous system are prone to have serious side effects (Carek, P. J. & Dickerson, L. M., "Current concepts in the pharmacological management of obesity," Drugs, vol. 57, pp. 883-904 (1999), which is incorporated herein by reference in its entirety).

Second, substances capable of affecting fat metabolism and storage will be more likely to act at peripheral sites. Adipocyte modulation occurs primarily through signals other than neurotransmitters, although many of these factors also have a multiplicity of effects on a variety of cells. In general, the more specific the cell spectrum and effect, the less likely there are to be untoward side effects.

Third, reduction in the fat depot, particularly visceral fat, has many beneficial medical consequences. It is now well established that in determining the risk of an individual developing certain metabolic sequelae, the distribution of body fat is of greater importance than the degree of excess adipose tissue per se. Upper body or visceral obesity is closely associated with cardiovascular disease, diabetes type II, and syndrome X (Anonymous, "Overweight, Obesity, and Health Risk," Archives of Internal Medicine, vol. 160, pp. 898-904 (2000), which is incorporated herein by reference in its entirety). In contrast, individuals with comparable amounts of adipose tissue stored in the femoral or gluteal depot (lower body obesity) have much lower risk for morbidity and mortality from the above-mentioned metabolic syndromes. It has been shown that the selective reduction in visceral adiposity with diet and exercise is accompanied by improvements in intermediary metabolism (Fujioka S., Matsuzawa Y., Tokunaga K., Kawamoto T., Kobatake T., Keno Y., Kotani K., Yoshida S. & Tarui S., "Improvement of glucose and lipid metabolism associated with selective reduction of intra-abdominal visceral fat in premenopausal women with visceral fat obesity," Int. Journal Obesity, vol. 15, pp. 853-9 (1991), which is incorporated herein by reference in its entirety).

In 1998, we observed the presence of large quantities of a 24 kDa proteoglycan in the urine of a patient diagnosed with pancreatic cancer. (Proteoglycans are a class of glycoproteins of high molecular weight that are found especially in the extracellular matrix of connective tissue.) The patient had lost almost 50 lbs over several months. Soon after this observation, we developed a sodium dodecyl sulfate-polyacrylamide gel electrophoresis (SDS-PAGE) method to purify the proteoglycan from the urine of the patient in milligram quantities. Administration of the proteoglycan to mice caused profound weight loss similar to the human subject. On autopsy of the mice receiving the proteoglycan, it appeared that the weight loss was primarily through depletion of intraperitoneal fat. There are epidemiologic studies that support the relationship between the abundance of intraperitoneal fat and the ill-effects of obesity (Lafontan, M. & Berlan M., "Do regional differences in adipocyte biology provide new pathophysiological insights?" Trends in Pharmacological Sciences, vol. 24, Issue 6, pp. 276-283 (2003), which is incorporated herein by reference in its entirety). Although there may be some advantage to decreasing intraperitoneal fat depots primarily, the beneficial effects of weight loss in humans seem to correlate with total fat loss (McCarthy, W. J., Arpawong, T. E., Dietsch, B. J., & Yancey, A. K., "Effects of exercise and weight loss on hypertension," JAMA, vol. 290, pp. 885-886 (2003); Redmon, J. B., Raatz, S. K., Reck, K. P., Swanson, J. E., Kwong, C. A., Fan, Q., Thomas, W., & Bantle, J. P., "One-year outcome of a combination of weight loss therapies for subjects with type 2 diabetes: a randomized trial," Diabetes Care, vol. 26, pp. 2505-11 (2003); The Look AHEAD Research Group, "Look AHEAD (Action for Health in Diabetes): design and methods for a clinical trial of weight loss for the prevention of cardiovascular disease in type 2 diabetes," Control Clin. Trials, vol. 24, pp. 610-28 (2003), all of which are incorporated herein by reference in their entireties).

Further studies revealed that the proteoglycan did not affect appetite or cause muscle loss in mice (see Figueroa, J. E., Vijayagopal, P., Debata, C., Prasad, A. & Prasad, C., "Azaftig, a urinary proteoglycan from a cachectic cancer patient, causes profound weight loss in mice." Life Sci. 64:1339-1347 (1999); Figueroa, J. E., Vijayagopal, P, Prasad, A., Schapira, D. V. and Prasad, C., "Isolation, characterization, and distribution of a 24-kDa proteoglycan in the urine of cachectic cancer and AIDS patients." Biochem. Biophys. Res. Commun. 254:642-46 (1999), which are both incorporated herein in their entireties). Because the proteoglycan caused selective depletion of the fat depot, we named it "azaftig" (or anti-zaftig—zaftig meaning fat or juicy in Yiddish language). In subsequent studies, we demonstrated a preponderance of azaftig in the urine of a variety of cancer and AIDS patients experiencing weight loss, but not in control subjects. These observations formed the basis of U.S. Pat. No. 6,274,550, which is incorporated herein by reference in its entirety.

We then examined the effect of protein isolated from the urine of patients experiencing weight loss on in vitro lipolysis by adipocytes isolated from obese Zucker rats and obese human subjects. The results of these studies showed a dose-dependent augmentation of lipolysis in both rat- and human-derived adipocytes (see Figueroa, J. E., Vijayagopal, P., & Prasad, C. 2002. Azaftig stimulates in vitro lipolysis by rodent and human adipocytes. Biochemical and Biophysical Research Communications. 293:847-49, which is incorporated herein by reference in its entirety). This protein was thought to be azaftig.

Several models of lipolysis have been elucidated. In the classical model (illustrated in FIG. 9(a)), a stimulus or agonist acts at the receptor (R) level to activate adenylate cyclase (AC) on the membrane of the cell. Activated AC catalyzes the conversion of ATP to cyclic AMP (cAMP). This second messenger (cAMP) causes the conversion of inactive protein kinase A (iPKA) to its active form (aPKA). This activated enzyme (aPKA) phosphorylates a wide variety of molecules including hormone sensitive lipase (HSL) and perilipin (Peri). (P=Phosphate in FIG. 9.) The inactive form of HSL (aHSL) is in the cytoplasm of the adipocyte. Once it is phosphorylated, this activated form (aHSL) moves to the lipid droplet and begins lipolysis. Perilipin, a molecule that coats the outer surface of the lipid droplet in the adipocyte, protects the lipid droplet against aHSL. However, once aPKA phosphylates Peri on the lipid droplet, Peri moves from the droplet to the cytoplasm. Therefore, the droplet is exposed to the action of aHSL. The aHSL, at this point, catalyzes the hydrolysis of triglycerides (TG) in the fat droplet to monoglycerides (MG) and free fatty acids (FFA). MG is further degraded into FFA and glycerol (G).

The amount of HSL activity correlates with the amount of HSL mRNA made and the degree of HSL protein modifications (such as phosphorylation, as discussed above). In general, HSL gene expression and activity vary with cAMP levels and PKA activation. Beta-adrenergic receptor stimulation is thought to be the most important event in PKA activation in adipocytes. Therefore, in the classical model, lipolysis correlates directly with cAMP levels and PKA activation. (For a review of the classical model, see Holm, C., Østerlund, T., Laurell, H., & Contreras, J. A., "Molecular mechanisms regulating hormone sensitive lipase and lipolysis." Annu. Rev. Nutr., 20:365-93 (2000), which is incorporated herein by reference in its entirety.)

Two recent lines of evidence challenge the classical model. The first line of evidence disputes the primacy of the cAMP-PKA system as the major signal transduction pathway in lipolysis. It has been demonstrated that natriuretic peptides (NP) stimulate lipolysis in macaque and human adipocytes through the cGMP-dependent receptor-mediated pathway (Sengenes, C., Berlan, M., De Glisezinski, I., Lafontan, M., & Galitzky, J., "Natriuretic peptides: a new lipolytic pathway in human adipocytes," FASEB J. July, 14(10):1345-51 (2000); Sengenes, C., Zakaroff-Girard, A., Moulin, A., Berlan, M., Bouloumie, A., Lafontan, M., & Galitzky, J., "Natriuretic peptide-dependent lipolysis in fat cells is a primate specificity," Am. J. Physiol. Regul. Integr. Comp. Physiol., July, 283(1):R257-65 (2002), both of which are incorporated by reference herein in their entireties). Briefly, instead of the stimulus causing changes in cAMP through AC, NP causes increases in cyclic GMP (cGMP) through the enzyme, guanylate cyclase (GC) (see FIG. 9(b)). High cGMP levels activate another protein kinase, protein kinase G (PKG). This activated enzyme (aPKG) then phosphorylates the same proteins as in the classical model (HSL and Peri) with the same effect. This stimulatory effect is roughly equivalent to that of beta-adrenergic agonists in these cells.

Other cAMP-independent pathways have also recently been implicated in lipolysis. These include the protein kinase C (PKC) (illustrated in FIG. 9(c)) and the calcium-dependent kinase pathways (illustrated in FIG. 9(d)). In the PKC model, a receptor-mediated phenomenon converts phospholipids (PL) to diacylglycerol (DAG) (Greenberg, A. S., Shen, W., Muliro, K., Patel, S., Souza, S. C., Roth, R. A., & Kraemer, F. B., "Stimulation of Lipolysis and Hormone-sensitive Lipase via the Extracellular Signal-regulated Kinase Pathway," J. Biol. Chem., 276: 45456-45461 (2001), which is incorporated by reference herein in its entirety). This conversion activates PKC, which subsequently phosphorylates proteins (including MAP Kinase (MAPK)) leading to lipolysis. The same is true with the calcium-dependent pathways involving vitamin D (Vit D) which causes changes in intracellular calcium (Ca++) leading to calcium-modulated protein kinase (CaMPK), phosphorylation of proteins, and lipolysis (see FIG. 9(d)) (Shi, H., Norman, A. W., Okamura, W. H., Sen, A., & Zemel, M. B., "1alpha,25-Dihydroxyvitamin D3 modulates human adipocyte metabolism via nongenomic action," FASEB J. 15:2751-2753 (2001); Shi, H., Norman, A. W., Okamura W. H. & Zemel, M. B., "1alpha,25-dihyroxyvitamin D3 modulates human adipocyte metabolism via nongenomic action," FASEB J. 15, 2751-2753 (2001)). These illustrations demonstrate that lipolysis can be stimulated through a variety of pathways that ultimately end in the phosphorylation of HSL and Peri. Those events, in turn, lead to lipolysis. In these models, HSL and Peri act as the control points for lipolysis.

The primacy of HSL in lipolysis has recently been challenged. Three independent groups have developed transgenic mice lacking the HSL gene (Haemmerle, G., Zimmermann, R., Hayn, M., Theussl, C., Waeg, G., Wagner, E., Sattler, W., Magin, T. M., Wagner, E. F., & Zechner, R., "Hormone-sensitive lipase deficiency in mice causes diglyceride accumulation in adipose tissue, muscle, and testis," J. Biol. Chem. February 15, 277(7):4806-15 (2002); Osuga, J., Ishibashi, S., Oka, T., Yagyu, H., Tozawa, R., Fujimoto, A., Shionoiri, F., Yahagi, N., Kraemer, F. B., Tsutsumi, O., & Yamada, N., "Targeted disruption of hormone-sensitive lipase results in male sterility and adipocyte hypertrophy, but not in obesity," Proc. Natl. Acad. Sci. USA. Jan 18, 97(2):787-92 (2000); Wang, S. P., Laurin, N., Himms-Hagen, J., Rudnicki, M. A., Levy, E., Robert, M. F., Pan, L., Oligny, L., & Mitchell, G. A., "The adipose tissue phenotype of hormone-sensitive lipase deficiency in mice," Obes. Res. February, 9(2):119-28 (2001), all of which are incorporated herein in their entireties). Unexpectedly, these mice were found to be phenotypically normal in most respects. The major phenotypic difference between HSL−/− mice and HSL+/+ mice was oligospermia (low sperm count). This finding confirms the importance of HSL as the neutral cholesterol ester hydrolase (NCEH) in testicular cells. Prior to the HSL knockout mice, HSL was thought to be the protein with NCEH activity. The fact that HSL knockout mice lack NCEH activity demonstrates that the knockout model does indeed eliminate HSL. Therefore, any lipolysis seen in these knockout mice is not due to HSL. Upon careful examination of all tissues, HSL−/− mice were found to lack NCEH activities in both brown adipose tissue (BAT) and white adipose tissue (WAT). (BAT is a small portion of total fat content but is largely responsible for the maintenance of body temperature. The amount of this fat decreases as the animal ages. WAT is the vast majority of the fat depot and is the major storage site for excess calories.) Additionally, both BAT and WAT adipocytes from HSL −/− mice were significantly larger in size than the corresponding adipocytes from wild type mice. The BAT mass was increased by about 50%, but the WAT mass remained unchanged. Interestingly, HSL−/− mice were neither obese nor cold intolerant. Lipase activity in WAT adipocytes was reduced only by 50% to 60% in HSL −/− mice. This means that, in addition to HSL, there is another lipase responsible for WAT lipolysis. As discussed below, adipomodulin has the ability to stimulate lipolysis in the absence of HSL. Thus, adipomodulin appears to work through regulation of a novel lipase (see FIG. 9(e)). (It is possible that adipomodulin works through a different pathway than the pathway shown in FIG. 9(e), although this is unlikely based on the increase in lipolysis in the absence of HSL. However, it is possible that adipomodulin causes de-repression of basal lipolysis activity. De-repression is the situation where the pathway has a natural inhibitor that is decreased by some stimulus. The release of that pathway's negative regulation causes more lipolysis. As an example, adipomodulin could affect only the amount of perilipin on the fat droplet. Because the amount of perilipin protects the fat depot, we might see more lipolysis without changes in the lipase activity.)

We have discovered a protein with a molecular weight of about 25 kDa to about 30 kDa which belongs to a family of light chains capable of binding to adipocytes to promote lipolysis, which appears to be stimulated through an HSL-independent pathway. Unlike azaftig, the protein is not a proteoglycan. We call the protein adipomodulin.

Immunoglobulins are proteins produced by B cells and plasma cells in mammals to fight infection. They are large molecules (about 150 kDa) composed of two separate types of polypeptide chains—one about 50 kDa (heavy or H chain) and the other about 25 kDa (light or L chain). The mature immunoglobulin molecule contains two H and two L chains. The two chains are present in equimolar ratios in the immunoglobulin molecule in pairs.

Figure 8:
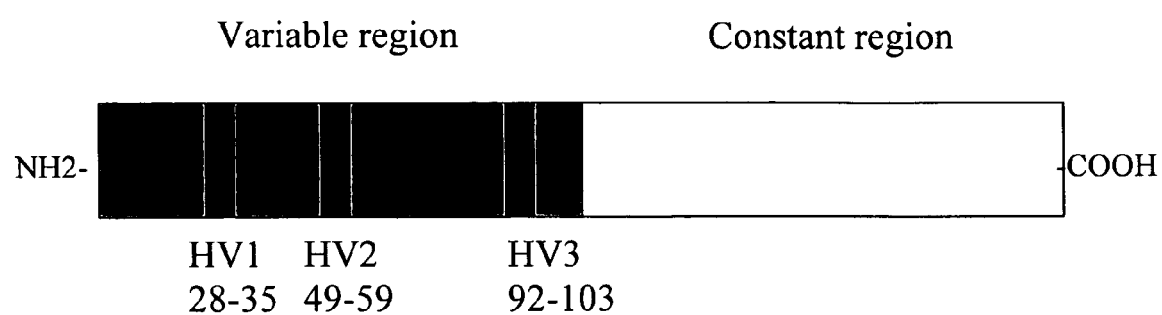
FIG. 8 is a schematic representation of the amino acid sequence of the light chain molecule [SEQ ID NO: 3].
Figure 9A:
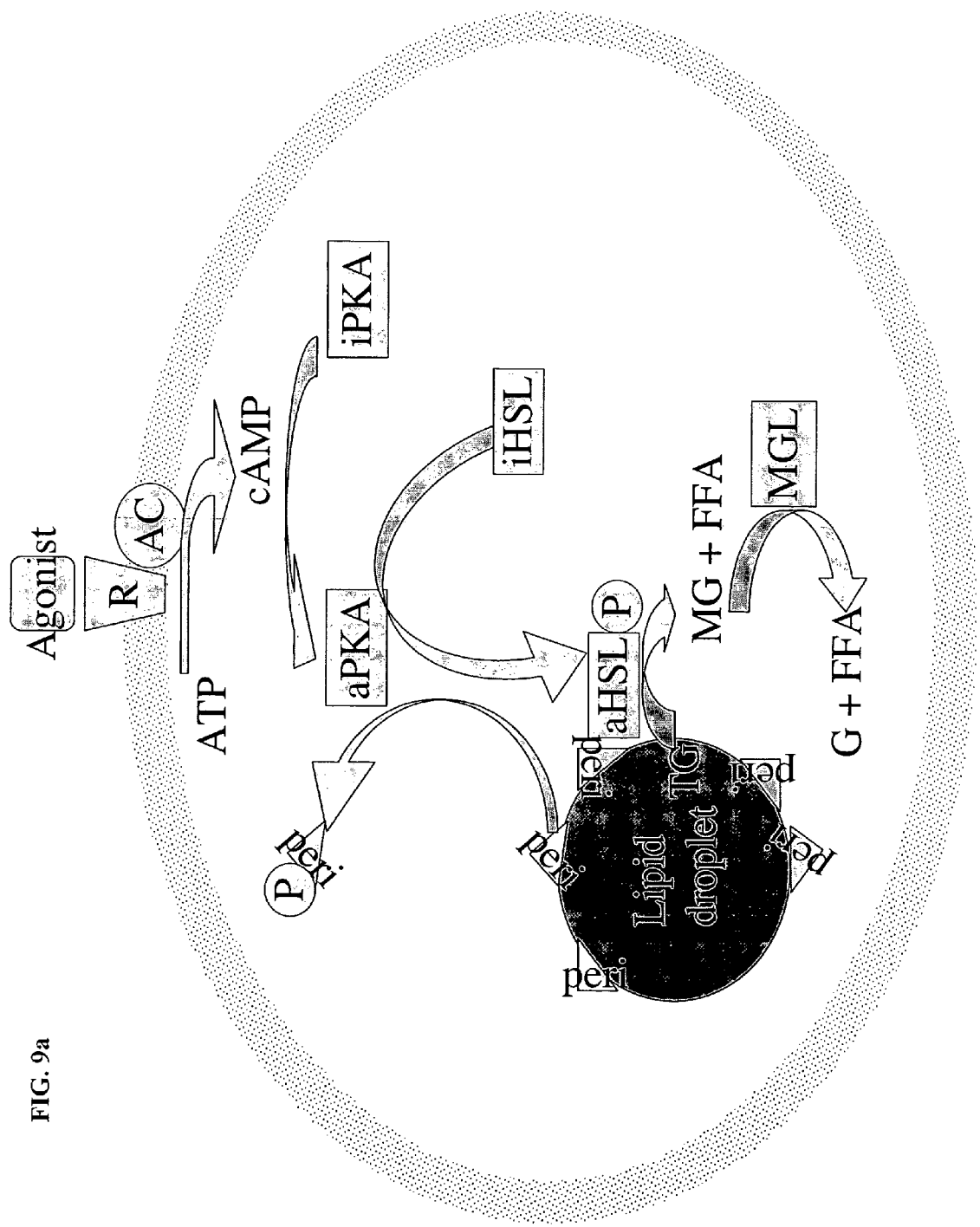
Figure 9B:
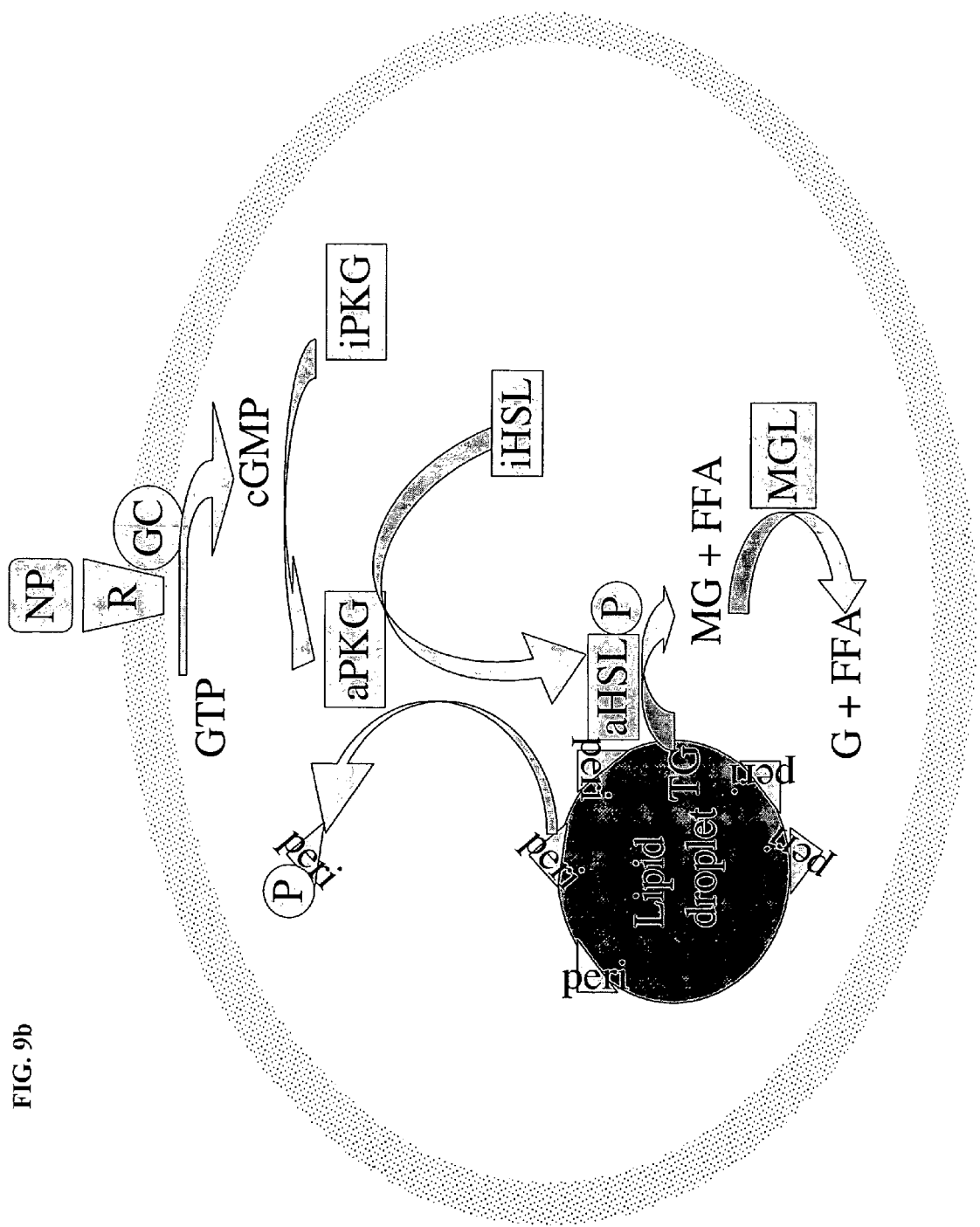
Figure 9C:
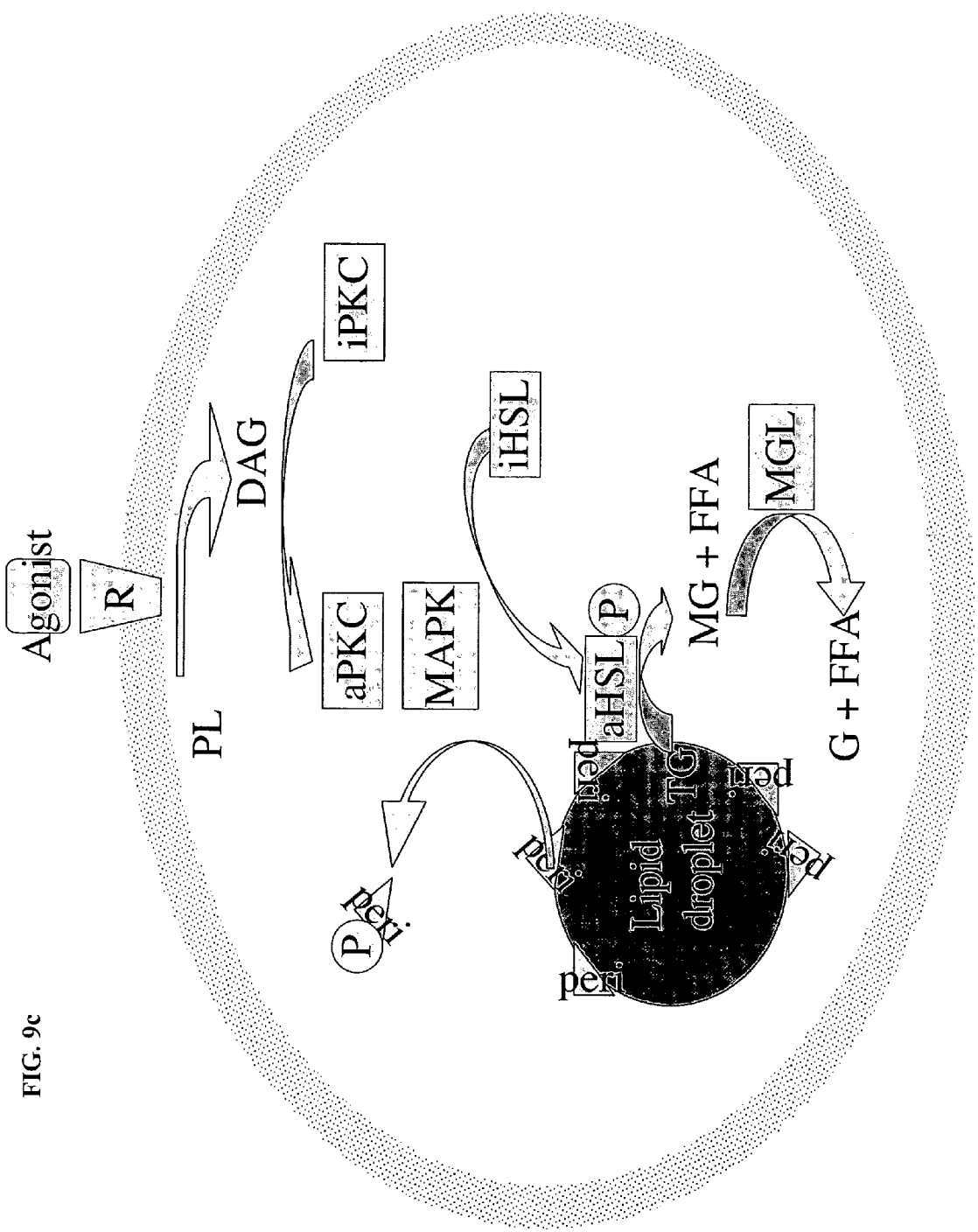
Figure 9D:
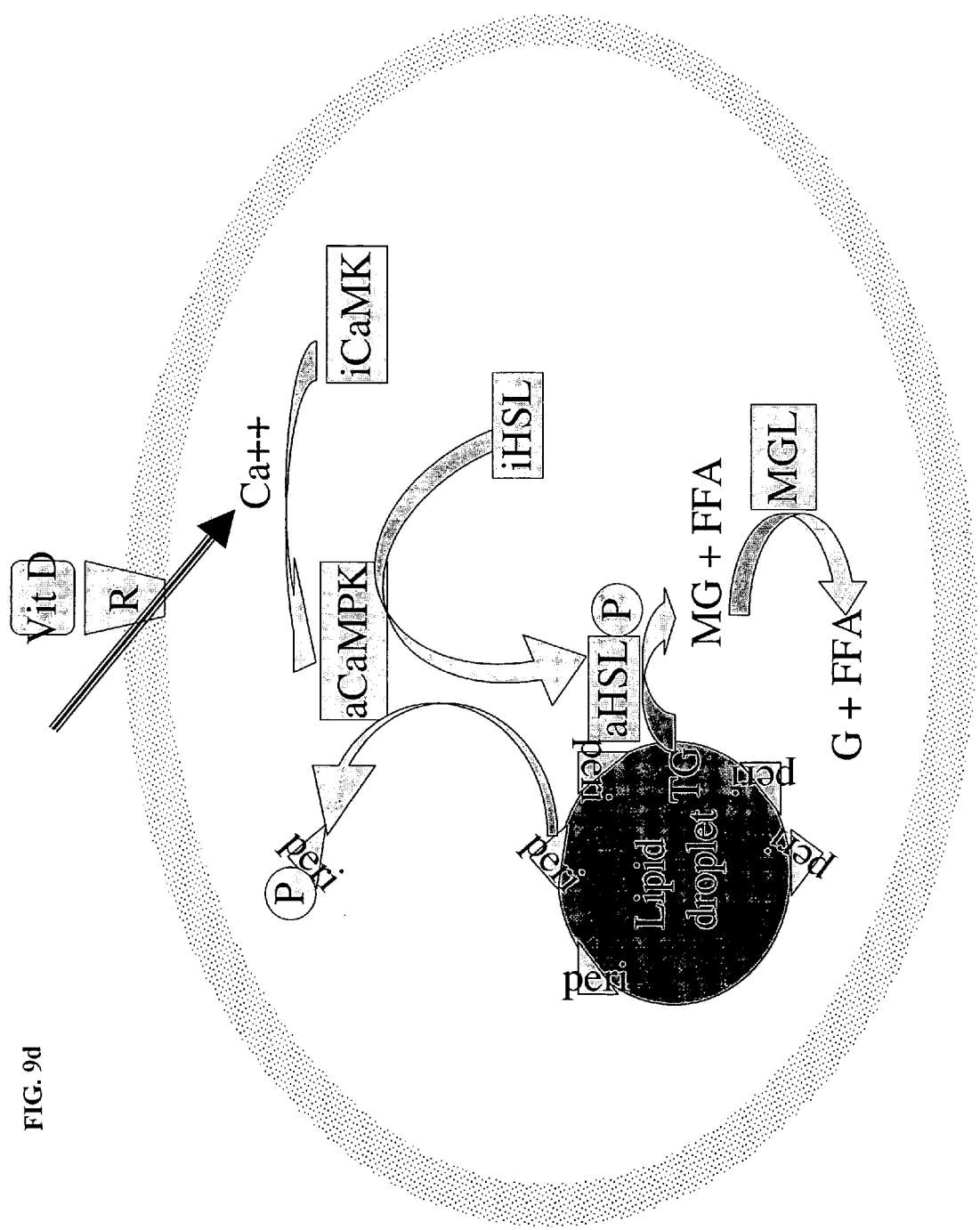
Figure 9E:
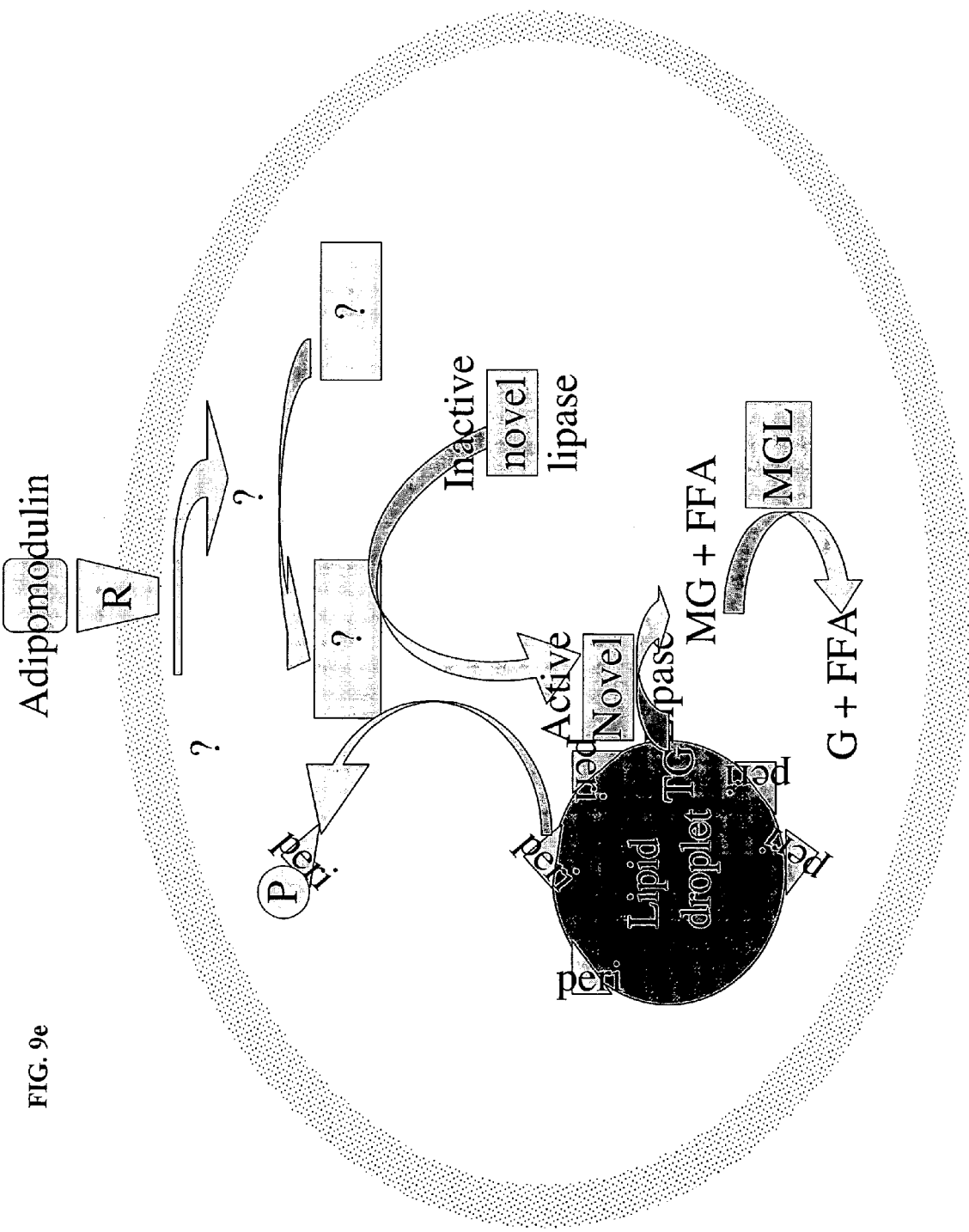

The H and L chains have variable and constant domains (see FIG. 8). Within the variable domains of both the H and L chains, there are three hyper variable (HV) domains which exhibit a high degree of variability. This variability accounts for the ability of the animal to produce antibodies to a wide variety of antigens. Each antibody molecule has a specific epitope that it recognizes. The epitope may be present on a variety of molecules both in the animal and in foreign antigens. This is the basis of the cross-reactivity of antibodies to a number of different antigens.

Several L chains have been described that bind specific tissues or cell components. This binding leads to specific effects in the tissue or cell. The consequences of such interactions are dependent on the nature of the L chain and the cell mechanism involved. For example, L chains can bind thyroid tissue to stimulate the gland to produce more thyroid hormone. The binding specificity of the L chain (and therefore its specific effect) is determined by the variability found in the variable region of the molecule, which is the first half of the molecule, particularly in the HV domains. Three dimensional structural analysis of the L chain places the HV domains in peptide loops that are in close proximity to each other. The peptide loops form the basis of the antigen-recognition site for the molecule by forming a surface complimentary to the antigen. Thus, the binding specificity of the L chain for any antigen largely resides in the configuration of the L chain's HV regions. Accordingly, to define the determinants of L chain binding to any antigen, one must define the L chain sequence in the HV regions, and different HV sequences can yield binding to similar or identical antigens with similar results. (See William Paul, Fundamental Immunology, Fifth Edition, chapters 3, 4, and 5 (2003), which are incorporated herein by reference in their entireties.)

There are two types of L chains: lambda and kappa. Lambda and kappa chains are products of two different genes and are defined by differences in their primary structure. The generic L chain consists of about 230 amino acids with an amino terminus at the far left and carboxy terminus at the far right (see FIG. 2). The first half constitutes the variable (V) domain and the second half the constant (C) domain. The DNA sequences encoding the V and C domains of the L chain are separated by some considerable distance in the genome of all cells except for lymphocytes of B lineage. Each variable domain is encoded in two separate DNA segments. The first segment encodes the first 95 to 101 amino acids of the L chain and is termed a V gene segment. The second segment encodes the remainder of the variable domain (up to 13 amino acids) and is termed a joining or J gene segment. The joining of a V and a J gene segment creates a continuous piece of DNA encoding the whole of the light chain V region. Only a noncoding DNA separates the J gene segment from the C gene segment, and RNA splicing after transcription, not by DNA recombination, joins the two.

Diversity in the structure of the L chain can arise in many ways. First, the locus of the L chain has 40 functional V gene segments accompanied by a cluster of 5 J segments and a single C gene. Different combinations of gene segments in different rearrangement events can generate diversity. Second, diversity is introduced at the joints between the different gene segments as a result of the recombination process, which is the process of similar DNA molecules crossing over and forming new DNA combinations. Recombination happens in numerous genes in bacteria, plants, and animals. For example, it is a principal source of diversity in the major histocompatibility antigens. Antibody genes undergo this recombination which allows for many combinations of HV regions. Third, somatic hyper-mutation can introduce point mutations into rearranged variable region genes. Somatic mutations are changes in DNA sequences that occur in non-germ cell lines (which are not passed on to offspring). Several points in the human genome are known to be areas where mutations occur at a rate that is much higher than the norm. Usually these areas represent genes where diversity has a survival advantage. The immunoglobulin genes are such genes. (See William Paul, 2003.)

Sequence variability is not distributed evenly throughout the variable regions (the distribution of variable amino acids is illustrated in FIG. 8). A typical L chain is composed of variable and constant domains of roughly equal size. The three HV domains are from residues 28-35, from residues 49-59, and from residues 92-103. These HV domains are denoted HV1, HV2, and HV3.

The nature of antibody production is that the variable domains of light chain molecules stay fairly constant for any particular antigen specificity in different types of immunoglobulin molecules. The heavy chain domains switch from IgM to IgG or IgA or IgE.

Adipomodulin will be useful in the treatment of obesity and obesity-related disorders. In certain embodiments, such treatments will involve adipomodulin variants, fragments, and/or agents. As used herein, "variant" means a different intact light chain molecule that has adipomodulin activity. "Adipomodulin activity" as used herein means that the molecule binds to adipocytes to promote lipolysis in the manner of adipomodulin. Embodiments comprising adipomodulin variants can be designed using methods known in the art to have enhanced activity (e.g., improved receptor binding, longer half-life, or other desirable characteristics). As used herein, "fragment" means a portion of an adipomodulin molecule or variant that has adipomodulin activity. The term fragment includes analogues. Fragments can be used to improve on adipomodulin activity as well as enhance the mechanics of administration (e.g., oral preparation, subcutaneous). As used herein, "agent" means a modified adipomodulin or variant that has adipomodulin activity. The term agent includes combinations of adipomodulins, e.g., dimers or trimers. The use of agents can allow for slow release preparations, entirely new compounds with other activities, and antagonists.

Adipomodulin therapeutic agents (i.e., agents that cause a positive response in the body) can be produced in a number of different ways. For example, adipomodulin therapeutic agents can be produced in in vitro protein synthesis systems. There are at least two separate approaches. One such approach would be to give intact adipomodulin molecules to patients (e.g., by parenteral administration). For this purpose, adipomodulin could be isolated from humans or artificially produced (i.e., man-made) using methods known in the art (e.g., genetic engineering or protein synthesis). There are many examples where intact molecules produced in vitro as therapeutic agents have been administered to treat a variety of ailments. For example, Humulin® (human insulin) produced in *E. coli* has been administered successfully to treat diabetes (Chance, R. E., & Frank, B. H., "Research, development, production, and safety of biosynthetic human insulin," Diabetes Care, 16 Suppl 3:133-42 (1993), which is incorporated herein by reference in its entirety). Another example is the use of recombinant human parathyroid hormone (PTH) for treatment of osteoporosis (Vahle, J. L., Sato, M., Long, G. G., Young, J. K., Francis, P. C., Engelhardt, J. A., Westmore, M. S., Linda, Y., & Nold, J. B., "Skeletal changes in rats given daily subcutaneous injections of recombinant human parathyroid hormone (1-34) for 2 years and relevance to human safety," Toxicologic Pathology, 30(3):312-21 (2002), which is incorporated herein by reference in its entirety.) Several plasmid constructs have been developed to express variable domains of L chains or H chains in *E. coli*. These constructs have been used to create anti-DNA binding molecules to mimic systemic lupus. (For a review, see Jatinderpal Kalsi, Chelliah T. Ravirajan, Anisur Rahman, & David A. Isenberg, "Structure-function analysis and the molecular origins of anti-DNA antibodies in systemic lupus erythematosus," Exp. Rev. Mol. Med. 16 February, (1999) http://www-ermm.cbcu.cam.ac.uk/99000423h.htm, which is incorporated herein by reference in its entirety.) Additionally, adipomodulin variants and/or fragments could be introduced into modified antibody constructs made in vitro. For example, adipomodulin sequences could be "grafted" to antibody molecules, made in vitro, and administered by injection to patients.

A second approach would involve designing a gene therapy system to deliver the adipomodulin gene to the patients. Thus, the patients would produce adipomodulin themselves from the gene construct. Use of gene therapy for the treatment of a variety of genetic diseases is a very promising area of investigation in medicine. This approach has so far been used to treat diseases like muscular dystrophy (van Deutekom, J. C. & van Ommen, G. J., "Advances in Duchenne muscular dystrophy gene therapy," Nat. Rev. Genet. October, 4(10):774-83 (2003), which is incorporated herein by reference in its entirety) and mucopolysaccharidosis I (Zheng, Y., Rozengurt, N., Ryazantsev, S., Kohn, D. B., Satake, N., & Neufeld, E. F., "Treatment of the mouse model of mucopolysaccharidosis I with retrovirally transduced bone marrow," Mol. Genet. Metab. August, 79(4):233-44 (2003), which is incorporated herein by reference in its entirety). This initial success has opened the possibilities of the use of gene therapy for the treatment of metabolic diseases such as diabetes and obesity as well.

A variety of gene therapy approaches can be implemented. For example, an adipomodulin gene sequence can be introduced into a plasmid DNA construct. The DNA can be encased in liposomes and delivered to the individual intravenously. Another approach involves the introduction of adipomodulin DNA into one of a variety of viral transfer vectors (see Robbins, P. D. & Ghivizzani, S. C., "Viral vectors for gene therapy," Pharmacol. Ther. October, 80(1):35-47 (1998), which is incorporated herein by reference in its entirety). In either of these systems, one can manipulate the DNA sequences to modify the adipomodulin molecule expressed.

Adipomodulin variants, fragments, and agents will be useful in pharmaceutical compositions for treating obesity and obesity-related disorders. Such pharmaceutical compositions may be formulated in a conventional manner using one or more physiologically acceptable carriers or excipients. The carrier(s) must be acceptable in the sense that it is compatible with the other ingredients of the composition and is not deleterious to the recipient thereof.

The pharmaceutical composition will be administered by any suitable method including, but not being limited to, parenteral, e.g intravenous, intraperitoneal, intramuscular, subcutaneous, mucosal, e.g. oral, intranasal, intraocular.

For oral administration, the pharmaceutical preparation may be in liquid form, for example, solutions, syrups or suspensions, or in solid form as tablets, capsules and the like. For administration by inhalation, the compositions are conveniently delivered in the form of drops or aerosol sprays. For administration by injection, the formulations may be presented in unit dosage form, e.g., in ampoules or in multidose containers with an added preservative.

The dose of the conjugate of the invention to be administered will depend on the individual's age and health condition, and other parameters well known to physicians.

Development of useful fragments and agents will involve a number of approaches. For example, the variable region of the adipomodulin molecule can be sequenced. Two sequencing strategies can be used: Edman protein sequencing of adipomodulin fragments and MALDI-TOF (mass spectroscopy) of adipomodulin fragments. It will be important to obtain small enough fragments to provide the full sequence of the fragment molecule, because the sequencing modalities can only identify the complete amino acid sequence of peptide chains that are of a certain size (fewer than about 20 amino acids). Therefore, to have a total sequence, one would have to generate fragments that are small enough to completely sequence. It will also be important to have confirmation with fragments derived from another digestion to provide overlapping sequences with the first sequence. The overlapping of fragments allow the practitioner to know the order of the fragments in the intact molecule. It serves as a check as well to make sure that the sequence obtained is correct. After sequencing, peptide analogues will be constructed in vitro and tested for activity. Such constructs can be generated through in vitro protein expression systems or de novo peptide synthesis using methods known in the art. For example, adipomodulin peptide analogues can be produced by culturing cells transformed or transfected with a vector containing adipomodulin nucleic acid. The adipomodulin sequence, or portions thereof, may be produced by direct peptide synthesis using solid-phase techniques (see, e.g., Stewart et al., "Solid-Phase Peptide Synthesis," W.H. Freeman Co., San Francisco, Calif. (1969); Merrifield, J., Am. Chem. Soc., 85:2149-2154 (1963)). In vitro protein synthesis may be performed using manual techniques or by automation. Various portions of the adipomodulin analogue may be chemically synthesized separately and combined using chemical or enzymatic methods to produce the full-length adipomodulin analogue. Formulations of adipomodulin fragments or agents could be developed to target specific adipocytes. Adipocytes from different fat depots have different metabolic and gene expression profiles, and adipomodulin may work through a mechanism that is more active in a particular fat depot (e.g., visceral versus peripheral adipocytes). Thus, adipomodulin fragments or agents could be manufactured to target these cells specifically or preferentially.

Fragments, variants, and agents will comprise one or several of the HV regions. With the determination of the amino acid sequence important in adipomodulin activity, one can manipulate the structure of this core structure to modify its absorption through the gastrointestinal tract, release into the serum, half-life in serum, targeting of tissues, and timing of adipomodulin production. For example, gastrointestinal absorption can be modified by the design of slow-release formulations (see, e.g., De Brabander, C., Vervaet, C., & Remon, J. P., "Development and evaluation of sustained release mini-matrices prepared via hot melt extrusion," J. Control Release, April 29, 89(2):235-47 (2003), which is incorporated herein by reference in its entirety). Liposomal encapsulation can be modified (see, e.g., Katayama, K., Kato, Y., Onishi, H., Nagai, T., & Machida, Y., "Double liposomes: hypoglycemic effects of liposomal insulin on normal rats," Drug Dev. Ind. Pharm., August, 29(7):7 (2003), which is incorporated herein by reference in its entirety). The release of the substance into the system can be modified by designing slow-release formulations (see Boehm, B. O., "The therapeutic potential of somatostatin receptor ligands in the treatment of obesity and diabetes," Expert Opin. Investig. Drugs, September, 12(9):1501-9 (2003), which is incorporated herein by reference in its entirety); the amino acid sequence can be modified to manipulate the molecule's release into serum (see, e.g., Heller, S., "Insulin lispro: a useful advance in insulin therapy," Expert Opin. Pharmacother., August, 4(8): 1407-1 (2003), which is incorporated herein by reference in its entirety). The half-life in serum can be modified; the amino acid sequence can be modified to make the molecule resistant to enzymatic inactivation (see Fischer, P. M., "The Design, Synthesis and Application of Stereochemical and Directional Peptide Isomers: A Critical Review," Curr. Protein Pept. Sci., October, 4(5):339-356 (2003), which is incorporated herein by reference in its entirety); blocking molecular groups can be added on the molecule (see Hakansson, S., Viljanen, J., &

Broo, K. S., "Programmed delivery of novel functional groups to the alpha class glutathione transferases," Biochemistry, September 2,42(34):10260-8 (2003), which is incorporated herein by reference in its entirety). Tissues can be targeted—the expression of adipomodulin DNA contructs can be designed to make the protein in the most favorable tissues, for example, by using tissue specific DNA promoters that only allow the expression of the adipomodulin DNA in those tissues (see, e.g., Chyung, Y. H., Peng, P. D., & Kay, M. A., "System for simultaneous tissue-specific and disease-specific regulation of therapeutic gene expression," Hum. Gene Ther., September 1,14(13):1255-64 (2003), which is incorporated herein by reference in its entirety). The timing of adipomodulin expression can be altered, for example, by expression of adipomodulin DNA constructs under the regulation of specific inducible DNA promoters (see, e.g., Srour, M. A., Fechner, H., Wang, X., Siemetzki, U., Albert, T., Oldenburg, J., Hanfland, P., Poller, W., Brackmann, H. H., & Schwaab, R., "Regulation of human factor IX expression using doxycycline-inducible gene expression system," Thromb. Haemost., September, 90(3):398-40 (2003), which is incorporated herein by reference in its entirety).

Established scientific principles indicate that the constant domain (about 50% of the molecule) and a significant part of the variable region of adipomodulins will be similar to generic L chain. Adipomodulins will likely be similar to each other in the hypervariable regions in terms of their tertiary structure. However, they will not be identical in their 3D structure, and they will be quite different in the DNA or amino acid sequences that are responsible for their structure. The interaction between an antibody and its antigen is a matter of the 3D conformation and the characteristics of the binding site. That conformation is dependent on the way the amino acids interact to yield more complex structures that place the important amino acids in the binding site where they need to be for interaction with the antigen. The amino acids in the binding site itself probably are more specific for the antigen and, therefore, less likely to be different. However, different adipomodulins could bind the same antigen at different sites with similar or opposite effects, which adds another level of complexity. Finally, amino acid sequences are derived from DNA sequences. There are generally different DNA triplet sequences that can yield the same amino acid in the protein. Therefore, one can have substantially different DNA sequences yielding the same or a very similar protein sequence. Moreover, it is certainly possible that different adipomodulins bind at different sites on the same or similar receptors yielding the same effects (i.e., lipolysis) with different adipomodulin protein structures.

Because adipomodulin is a protein natural to the body, it will be safe, avoiding complications associated with other treatments and types of drugs known in the art used in the treatment of obesity.

Adipomodulins, variants, and/or fragments may be combined or clustered together to create the lipolysis effect. For example, dimers, trimers, etc., may be more potent than the individual adipomodulin molecule by itself. In fact, a single 25-30 kDa molecule of adipomodulin may naturally complex with another to give the activity we see.

We isolated adipomodulins from the urine of individuals experiencing chronic inflammation and significant weight loss ("significant weight loss" as used herein means loss of more than about 3% of body weight). "Isolated" means adipomodulin has been identified and separated and/or recovered from a component of its natural environment.

The appearance of adipomodulin in the urine is likely related to generalized renal dysfunction seen in sick individuals with cancer, HIV, and other chronic inflammatory states. It is possible that an individual can produce adipomodulin in the serum but not have urinary excretion if renal function is intact. It is the adipomodulin in the serum that is contributing to the fat loss in these individuals. Therefore, adipomodulin can be isolated from test samples comprising urine and/or blood.

It is possible that individuals who produce adipomodulin are in fact having an autoimmune response to their own adipocytes. This autoimmune response (with the production of L chain +/− H chain to make intact antibody molecules) is inducing adipocyte lipolysis. These patients can be identified by the presence of significant weight loss in the face of chronic inflammation or cancer. In our survey, about 50% of patients with cancer or HIV and significant weight loss had adipomodulin in their urine. No individuals (patients with cancer or HIV, patients without cancer or HIV, and normal individuals) without weight loss had adipomodulin.

There are a number of methods that can be used to isolate adipomodulins from test samples taken from subjects. For example, Immuno-affinity chromatography can be used. Immuno-affinity chromatography is a method where anti-L chain antibodies are placed on a solid matrix and the material in question (urine in this case) can be passed through the column to capture L chains (Lim, A., Wally, J., Walsh, M. T., Skinner, M., & Costello, C. E., "Identification and location of a cysteinyl posttranslational modification in an amyloidogenic kappal light chain protein by electrospray ionization and matrix-assisted laser desorption/ionization mass spectrometry," Anal. Biochem., August 1,295(1):45-5 (2001); Siegel, D. L., "Selecting antibodies to cell-surface antigens using magnetic sorting techniques," Methods Mol. Biol., 178:219-26 (2002)). Other methods include, without limitation, different precipitation schemes followed by ion-exchange chromatography (L chains are usually charged) and then immuno-affinity chromatography (ibid.). Another approach would be a step-wise method from the blood of subjects who have chronic inflammation and significant weight loss. The first step would be to isolate the free L chains or intact antibody molecules from the test sample. Intact antibody molecules can be isolated using antibody-specific chromatography (e.g., using either protein A or protein G). Free L chains can also be isolated by ion-exchange chromatography or L chain specific immuno-affinity chromatography. These isolated molecules can then be assayed for their ability to bind to adipocyte membranes that have been crosslinked to solid matrix beads. Those molecules that bind can be tested for their ability to induce lipolysis in vitro assay to confirm them as adipomodulins or intact antibodies with adipomodulin activity. Similar techniques have been used to isolate thyroid stimulatory antibodies in patients with autoimmune hyperthyroidism (Rees, Smith B., & Hall, R., "Thyroid-stimulating immunoglobulins in Graves' disease," Lancet 2:427-431 (1974); Mehdi, S. Q. & Nussey, S. S., "A radio-ligand receptor assay for the long-acting thyroid stimulator," Biochem. J. 145:105-111 (1975); Rapoport, B., Chazenbalk, G. D., Jaume, J. C., & McLachlan, S. M., "The thyrotropin (TSH) receptor: interaction with TSH and autoantibodies," Endocr. Rev., 19: 673-716 (1997)).

Based on 2D gel electrophoresis pattern, we have one adipomodulin sample (from Patient 203) with one protein species. Based on HPLC using a C18 column, one adipomodulin sample (from Patient 122) had one minor species in addition to the major component. Another adipomodulin sample (from Patient 203) was pure.

EXAMPLE 1

Screening Urine for the Presence of Proteins Causing Enhancement of Lipolysis

Total protein was isolated from 24 hour urine of patients experiencing weight loss and screened for the presence of lipolysis-enhancing activity. The procedure was as follows: A 16 ml filtered urine sample was mixed with 4 volumes of saturated ammonium sulfate (in water). The sample was mixed gently overnight in cold room. Subsequently, the sample was centrifuged (10,000 g for 30 minutes) and the pellet was collected. The pellet was dissolved in a minimal volume of water, and the solution was dialyzed against 2 changes of 2 L water over a 24 hour period. The dialyzed sample was lyophilized and then resuspended in 0.5 ml of Kreb's Ringer bicarbonate buffer (KRB) containing 2% glucose, but no bovine serum albumin (BSA).

Preparations were assayed for lipolytic activity using rat adipocytes isolated from obese Zucker rats. (Zucker rats obtained for our studies were from the Department of Physiology, LSU Health Sciences Center colony. There are many commercial vendors who sell these rats, including Hilltop Lab Animals, Inc., Hilltop Drive, Scottdale, Pa. 15683; Charles River Laboratories, Inc., 251 Ballardvale Street, Wilmington, Mass. 01887 and Taconic, 273 Hover Avenue, Germantown, N.Y. 12526.) Isolation of adipocytes from fat tissues was performed by the method of Rodbell (see Rodbell, M., Metabolism of isolated fat cells, J. Biol. Chem., 239: 375-380 (1964), which is incorporated herein by reference in its entirety) with some minor modifications. Briefly, fat tissue was rinsed with warm saline, excess liquid blotted out, and tissue weighed. Each 2 g fat tissue was suspended in 3 ml KRB with 1% BSA containing 3 mg collagenase (Sigma, Cat# C-6885) and minced into small pieces with a scissor and digested at 37° C. for 30 minutes under vigorous shaking. After digestion, the cell suspension was filtered through a nylon filter (Spectrum Laboratories) and washed 3 times with KRB and 1% BSA by centrifuging at 500 RPM for 1 minute (Beckman table top centrifuge) to remove stromavascular fraction and collagenase. Isolated fat cells were resuspended in KRB with 4% BSA at the rate of 2 g of fat tissue per ml.

The procedure for the lipolysis assay was as follows: Adipocytes were incubated in 1.5 ml polytheylene microfuge tubes for 120 minutes with continuous gentle shaking in a water bath at 37° C. The reaction mixture contained 50 ul of adipocytes and increasing volumes of urinary protein preparation or urinary protein elution buffer; the total volume was made to 150 ul with KRB containing 2% glucose but no BSA. At the end of incubation, the reaction mixture was centrifuged (15,000 g for 20 seconds) and a portion of the bottom aqueous phase was withdrawn with a long 27 gauge needle without contaminating with adipocytes. The reaction was run for 2 hours at 37° C. The amount of glycerol released in the aqueous phase was measured by radiometric assay of glycerol using the method described in Bradley, D. C. & Kaslow, H. R., "Radiometric assays for glycerol, glucose and glycogen," Anal. Biochem. vol. 180, pp. 11-16 (1989), which is incorporated herein by reference in its entirety. The data are presented in FIG. 1.

In a screening of 13 urine samples taken from cancer patients experiencing significant weight loss (patients 105, 109, 114, 115, 116, 121, 122, 201, 202, 203, 204, 205, and 212) we found 7 samples to be positive for lipolysis enhancement. Of the seven positive urine samples, two samples (from patients 203 and 212) caused at least a doubling of lipolysis (320% and 260% over control lipolysis, respectively) at maximum concentration added in isolated rat adipocytes. Moreover, the positive samples exhibited a dose-dependent stimulation.

EXAMPLE 2

Potentiation of Lipolysis in Rat and Human Adipocytes

Figure 5:
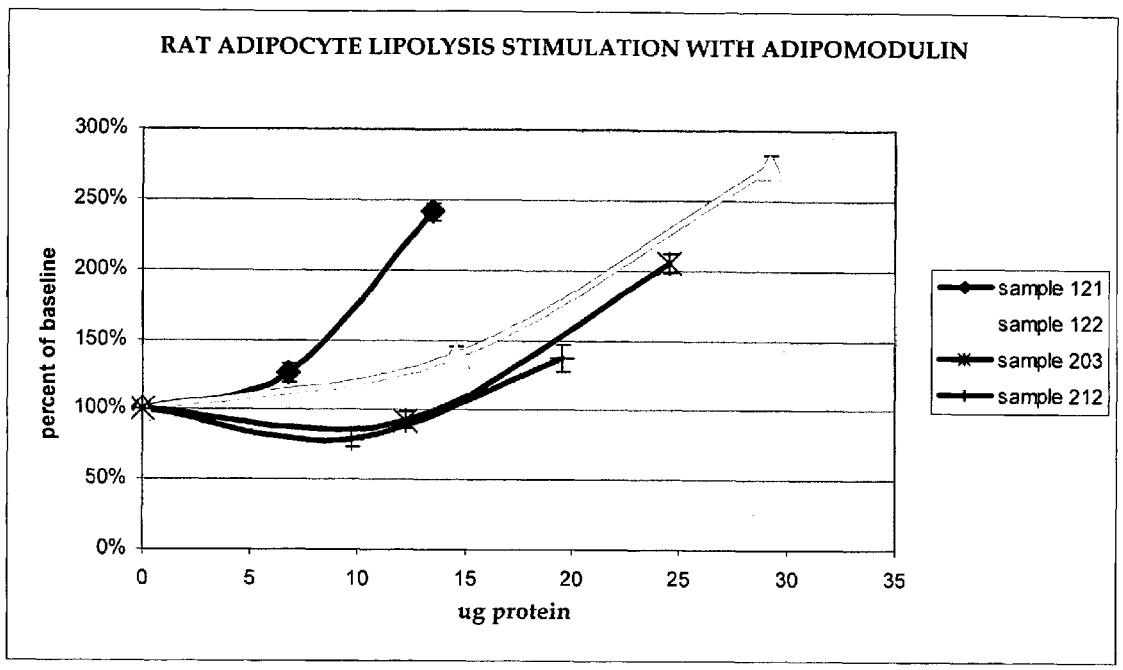
FIG. 5 is a graph of results for a lipolysis stimulation assay in rat adipocytes for adipomodulin.
Figure 6:
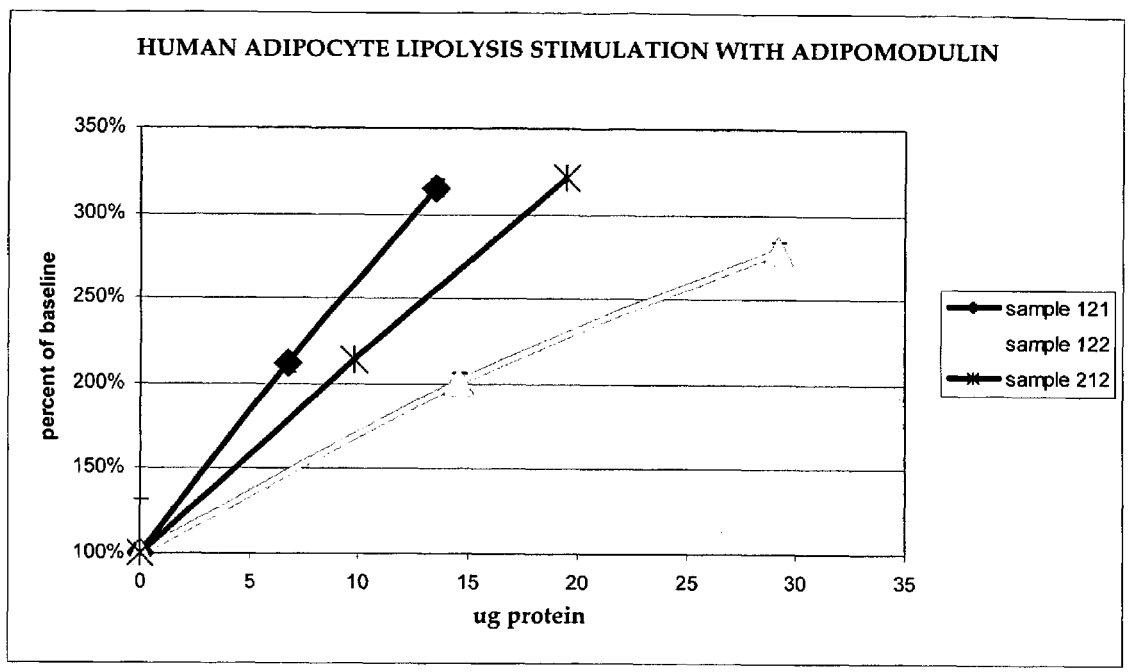
FIG. 6 is a graph of results for a lipolysis stimulation assay in human adipocytes for adipomodulin.

Specimens exhibiting positive lipolytic activity in the tests as described in Example 1 were further purified by SDS-PAGE on 15% gel along with molecular weight standards. At the end of electrophoresis, the standard lane was cut off the gels and a small strip was stained with coomassie blue. The stained gel was then aligned with the rest of the gel and the area corresponding to the 25-30 kDa band was cut. Proteins were extracted from the gel with 0.1% SDS in 50 mM ammonium acetate. Samples from four separate patients (patients 121, 122, 203, and 212) were prepared and tested on isolated rat and human adipocytes using the lipolysis assay procedures described in Example 1. (Human adipocytes were prepared from visceral fat obtained from three subjects undergoing elective bariatric surgery. Rat adipocytes were obtained from Zucker rats as described above in Example 1. Both human and rat adipocytes were isolated as described in Example 1.) The results of the lipolysis assay are shown in FIG. 5 (rat adipocytes) and FIG. 6 (human adipocytes). Each preparation caused a dose-dependent stimulation of lipolysis as compared with control cells, and each preparation exhibited very similar stimulation profiles with both rat and human adipocytes.

EXAMPLE 3

Structural Identity of Adipomodulin

Protein isolated from patient 122 (Sample 122) was subjected to Matrix-Assisted Laser Desorption Ionization (MALDI) ToF/ToF analysis by Applied Biosystems, MA. MALDI ToF/ToF is a method based on mass spectrometry used to determine the nature and partial amino acid sequence of proteins. This experiment demonstrated that the protein in Sample 122 was an L chain by partial determination of the amino acid sequence and comparison to generic L chain sequences. The results showed that structurally, Sample 122 was a light chain of the kappa type.

These results were confirmed by cross reacting Sample 122 with an anti-light chain antibody by Western blot assay: Proteins were separated by SDS-PAGE and transferred onto nitrocellulose filter paper. After transfer, the paper was exposed to antibodies to human light chains derived from rabbits. After extensive washing and incubation with antibodies to rabbit antibodies conjugated to alkaline phosphatase, the specific antibody binding was detected by a calorimetric reaction (Ed Harlow & David Lane, "Antibodies. A Laboratory Manual," pp. 471-510, Cold Spring Harbor Laboratory, Cold Spring Harbor, N.Y. (1988), which is incorporated by reference herein in its entirety).

EXAMPLE 4

Labeling of SDS-PAGE Purified Lipolysis Stimulating 25-30 kDa Urinary Proteins

Figure 3:
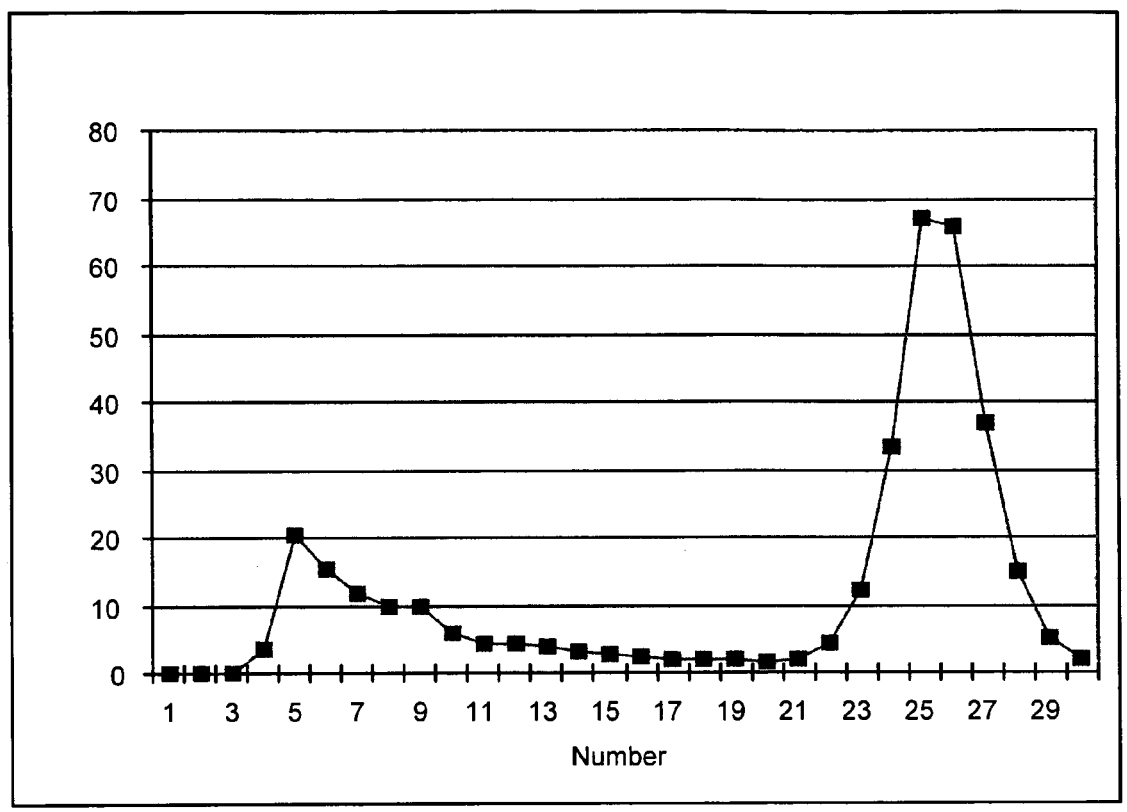
FIG. 3 is the elution profile of 125, labeled Sample 122.

To further examine the chemical nature of the protein in Sample 122, and protein from other samples, and their ability to bind to fat cells, the proteins were chemically labeled with $^{125}$Iodine as follows: 1 mCi $^{125}$I-Na (10 μl), 0.5 M sodium phosphate buffer (40 μl), and 10 μg of chloramine-T (20 μl) were added to a tube containing 1 μg of protein to be labeled (10 μl). The reaction was stopped after 45 seconds by adding 100 μl of (2.5 mg/ml) sodium thiosulfate. After addition of a 100 μl rinse solution (1 mg/ml KI and 8 mg/ml sucrose in water), the entire content of the tube was loaded on to a Sephadex G-10 (12×75 mm). The column was eluted with 50 mM sodium phosphate buffer, pH 7.5, and 30 fractions (1 ml) were collected. The radioactivity in each fraction was measured by counting a 5 μl sample. The results (presented in FIG. 3) show a typical elution pattern with two peaks at fractions 5-6 and 25-26. This shows that the proteins were properly labeled—the first peak is protein and the second peak is free iodine (see Greenwood, F. C., Hunter, W. L., & Glover J. J., "The preparation of $^{131}$I labeled growth hormone of high specific activity," Biochem. J., vol. 89, pp. 114-123 (1963), which is incorporated by reference herein in its entirety).

EXAMPLE 5

Enzymatic Digestion of $^{125}$I-Labeled Proteins

Purified $^{125}$I-labeled protein from patients 116, 121, 122, 203, and 212 was digested individually with neuraminidase (1.2 mUnits/ml in 0.5 M sodium acetate, pH 5.0 containing 20 mM $CaC_{12}$) for 16 hours at 37° C., chondroitinase ABC (2 Units/ml in 0.25 M Tris.HCl, pH 8.0) for 18 hours at 37° C., and chondroitinase AC (1 Unit/ml in 50 mM Tris.HCl, pH 8.0 containing 50 mM NaCl) for 18 hours at 37° C. The untreated control and the enzyme-digested materials were subjected to SDS-PAGE followed by autoradiography. Data for the protein preparations are summarized in FIG. 4. These results show that unlike azaftig, the protein in preparations 116, 121, 122, 203, and 212 were not proteoglycans, as is indicated by their resistance to digestion by chondroitinase AC and chondroitinase ABC. The proteins' resistance to digestion by neuraminidase indicates that these molecules do not comprise sialic acid.

EXAMPLE 6

Potentiation of Lipolysis in 3T3L1-Derived Adipocytes

NIH 3T3-L1 cells were obtained from American Type Culture Collection (Manassas, Va.). NIH 3T3-L1 cells are a mouse-derived fibroblast cell line that convert into adipocytes under certain conditions. This cell system is a standard model for the study of adipocyte metabolism. The cells were cultured in Dulbecco Modified Eagle's Medium (DMEM) (4500 mg glucose/liter) containing 10% fetal bovine serum. When the cells were 75% confluent, they were subcultured into multi-well culture plates and allowed to grow to confluency. The differentiation of the cells into adipocytes was initiated by the addition of 10 uM dexamethasone, 0.5 mM isobutyrylmethylxanthine, and 10 ug/ml insulin to the culture medium for 3 days, followed by the cultivation of the cells in culture medium without the supplements for an additional 3 or more days. The methods for the lipolysis assay were the same as described above in Examples 1 and 2.

Figure 7:
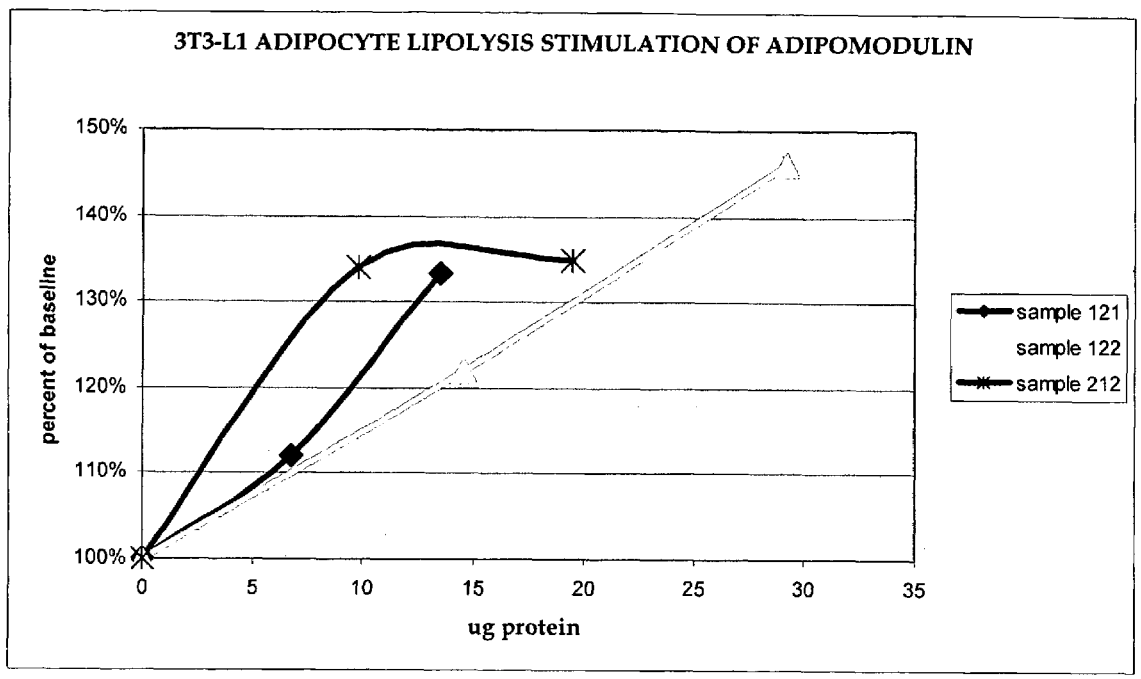
FIG. 7 is a graph of results for a lipolysis stimulation assay in 3T3-L1 cells for samples of adipomodulin.

The results with 3T3-L1 cells reflect less sensitivity of these cells to the same sample preparations used in the rat and human adipocyte experiments (see FIG. 7). This demonstrates that the 3T3-L1 cell system is a good model for the study of adipomodulin-mediated alteration in adipocyte metabolism. It also shows that the effect of adipomodulin is more pronounced in human-derived cells than in the 3T3-L1 cell system. Thus, it is expected that the changes seen in 3T3-L1 cells will be even greater in human cells.

EXAMPLE 7

Light Chain Assay

Although adipomodulins are immunoglobulin light chains, not all light chains promote lipolysis. We have two types of evidentiary support. First, we tested a commercially available generic kappa/lambda chain mixed preparation (Calbiochem, San Diego, Calif.; Cat# 401112, Lot # 39945) for its ability to modulate lipolysis in rat adipocytes. The procedure for the lipolysis was the same as described above in Example 1 & Example 2. The results are shown below in Table 2:

TABLE 2

| Sample Tested | Concentration(μg/assay) | Lipolysis (% of Basal) | p-Value |
|---|---|---|---|
| Light Chain | 21.0 | 106 ± 2 | >0.5 |
|  | 42.0 | 111 ± 4 | >0.5 |
| adipomodulin | 15.0 | 139 ± 7 | P = 0.045 |
| (Sample 122) | 30.0 | 275 ± 27 | P = 0.027 |

The results show that addition of 21 μg and 42 μg kappa/lambda chain mixed preparation to the assay mixture failed to promote a significant change in lipolysis by rat adipocytes. In contrast, the addition of 15 μg and 30 μg of an adipomodulin preparation (Sample 122) caused 139% and 275% stimulation of lipolysis, respectively.

Second, we collected 24-hour urine from a myeloma patient who had experienced no weight loss ("Patient A"). We isolated a 25-30 kDa protein from the urine using the procedures described above in Example 1. The results (which are summarized in Table 3) show that the 25-30 kDa preparation from Patient A, unlike preparations containing adipomodulin (from patients experiencing weight loss), did not exhibit in vitro lipolysis by rat adipocytes.

TABLE 3

| Sample tested | Concentration (μg/assay) | Lipolysis (% of Basal) | p-Value |
|---|---|---|---|
| 25-30 kDa preparation from myeloma patient | 20.0 | 94 ± 12 | >0.5 |
| adipomodulin | 15.0 | 139 ± 7 | P = 0.045 |
| (Sample 122) | 30.0 | 275 ± 27 | P = 0.027 |

On SDS-PAGE, the ammonium sulfate fraction, however, showed copious amounts of a 25-30 kDa material similar to the size of adipomodulin, which suggests the presence of light chain. The sample from Patient A was then subjected to sequence analysis by Edman's degradation method (see Heinrikson, R. L., "The Edman degradation in protein sequence analysis" in Biochemical and Biophysical Studies of Proteins and Nucleic Acids, T-B Lo et al., Eds. (Elsevier, New York, 1984), pp. 285-302, which is incorporated by reference herein in its entirety). The results showed that the sample from Patient A contained two peptides with the following amino-terminal sequences:

DIQMT QSPSS . . . . . . . . . . . . . . . . . . [SEQ ID NO: 1]
EIVLT QSPGT . . . . . . . . . . . . . . . . [SEQ ID NO: 2]

Both of these sequences have a high degree of homology with kappa light chain. Thus, it appears that Patient A had a kappa chain secreting myeloma. However, this light chain was apparently not capable of promoting lipolysis.

EXAMPLE 8

Adipomodulin Stimulates Lipolysis in NIH 3T3-L1 Adipocytes without Increasing Camp Levels Stimulation of lipolysis in differentiated 3T3-L1 cells was measured according to the procedure described in Hirsch, A. H. & Rosen, O. M., "Lipolytic stimulation modulates the subcellular distribution of hormone-sensitive lipase in 3T3-L1 cells," J. Lipid Res., vol. 25, pp. 665-667 (1984), which is incorporated herein in its entirety. The 3T3-L1 preadipocyte cell line (from ATCC) was differentiated by treating confluent monolayers with dexamethasone 0.5 µM, 0.15 µM insulin, and methylisobutylxanthine (IBMX) 0.5 mM. After 48 hours, the cells were fed with fresh medium containing 0.15 µM insulin and maintained in culture for 24 hours. Next, the cells were maintained in insulin-free DMEM containing 10% fetal bovine serum for 4-5 days. On the day of experimentation, the differentiated cells were incubated in serum-free DMEM containing 0.2% fatty acid free BSA and 5 mM glucose and treated with adipomodulin, adipomodulin elution buffer, or IBMX at 37° C. for 4 hours. At the end of incubation, 0.01 ml of supernatant was removed for glycerol assay using the radiometric assay of Bradley and Kaslow, as modified by Brasaemle in Brasaemle, D. L., Levin, D. M., Adler-Wailes, D. C., & Londos, C., "The lipolytic stimulation of 3T3-L1 adipocytes promotes the translocation of hormone-sensitive lipase to the surfaces of lipid storage droplets," Bioch. Biophys. Acta., Jan. 17, 1483(2):251-262 (2000), which is incorporated herein in its entirety. The cAMP assay for both supernatant and cytosol were performed according to the manufacturer's instructions (Amersham): The cells and their media (supernatant) were harvested separately. The cAMP was extracted from the cell cytosol with 70% ethanol. The levels of cAMP in the cytosol and the supernatant were measured by competitive radioimmunoassay. Briefly, this assay contains radioactive cAMP and a small amount of an antibody that recognizes cAMP (enough to bind about 10% to about 20% of the radioactive cAMP added). After several washing steps, the complexes of radioactive cAMP-antibody are counted in a gamma counter. To this system, known amounts of unlabeled cAMP are added, and the unlabeled cAMP competes with the radioactive cAMP for binding to the antibody in a dose-dependent manner. This relationship, therefore, allows for the determination of cAMP levels in test samples. Table 4 shows the cAMP levels after each treatment.

TABLE 4

| Treatment | cAMP, fmol/well | Lipolysis (pmol glycerol/well) |
|---|---|---|
| Elution buffer, 50 ul | 35 ± 2 | 1200 ± 200 |
| Elution buffer, 100 ul | 32 ± 3 | 600 ± 100 |
| Culture medium, 100 ul | 45 ± 2 | 1050 ± 250 |
| Sample 122, 15 ug | 17 ± 1 | 1800 ± 100 |
| Sample 122, 30 ug | 12 ± 1 | 1900 ± 50 |
| IBMX, 0.1 mM | 69 ± 4 | 3400 ± 50 |

As expected, IBMX showed a significant stimulation of cAMP over medium control and elution buffer controls. IBMX is a drug that inhibits the degradation of cAMP. Therefore, cAMP accumulates in the cells in the presence of IBMX. Elution buffer had a modest inhibitory effect on cAMP despite a significant stimulation of lipolysis. Adipomodulin (Sample 122) had little effect on cAMP. As noted, the classical pathway for lipolysis involves the formation of cAMP that in turn leads to other downstream events resulting in lipolysis. The above experiment demonstrates that adipomodulin does not work through this pathway and, therefore, is unique among lipolytic agents.

EXAMPLE 9

Adipomodulin Stimulates Lipolysis in HSL −/− Adipocytes

To determine whether adipomodulin acts through the classical HSL pathway, Sample 121 was tested in HSL+/+ and HSL−/− adipocytes derived from wild type and HSL knock-out mice (obtained from Dr. Grant Mitchell, Sainte Justine Hospital, Montreal, Quebec, Canada), respectively. Using methods known in the art (see Wang, S. P., Laurin, N., Himms-Hagen, J., Rudnicki, M. A., Levy, E., Robert, M. F., Pan, L., Oligny, L., & Mitchell, G. A., "The adipose tissue phenotype of hormone-sensitive lipase deficiency in mice," Obes. Res., February, 9(2):119-128 (2001), which is incorporated herein in its entirety), 10 µg of Sample 121 was compared with control buffer, an inactive kappa protein, and known stimulators of HSL-mediated lipolysis (isoproterenol, CL316y,243 (a beta-3 adrenergic agonist), and dibutryl cAMP). Lipolysis was measured as glycerol release from an adipocyte suspension. In each experiment, adipocytes were pooled from perigonadal fat of two to four 6-month-old mice of the same gender and genotype. One hundred microliters of adipocyte suspension were incubated for 2 hours in a final volume of 500 mL of Krebs-Ringer-HEPES (30 mM) buffer (pH 7.4) supplemented with 2.5% BSA, 2.5% N6-[R-(−)-1-methyl-2-phenyl] adenosine (10 mM), and 1 U/mL adenosine deaminase. In some tubes, the lipolytic beta3-adrenergic agonist CL316,243 (10 mM) (Wyeth-Ayerst Research Laboratories, Princeton, N.J.) or cAMP agonist (dibutryl cAMP) were added. After a 2-hour incubation, the reaction was stopped by freezing on dry ice. The mixture was extracted with chloroform to remove triglycerides, and glycerol content was then determined by glycerol assay kit (Roche Diagnostics).

The results of two such experiments are shown in Table 5; it can be seen that Sample 121 stimulated lipolysis equally in both HSL+/+ and HSL−/− adipocytes (about a two-fold increase over baseline).

TABLE 5

| | Lipolysis (nmol glycerol produced) | |
|---|---|---|
| Treatment | HSL +/+ | HSL −/− |
| Basal | 0.1 ± 0.02 | 0.4 ± 0.1 |
| Isoproterenol, 10 uM | 5.8 ± 1.0 | 0.9 ± 0.2 |
| CL316, 243, 10 uM | 6.2 ± 1.1 | 1.1 ± 0.3 |
| Dibutryl cAMP, 1 mM | 7.6 ± 1.0 | 1.1 ± 0.1 |
| Sample-control | 0.4 ± 0.02 | 1.0 ± 0.1 |
| adipomodulin (Sample 121) | 1.9 ± 0.2 | 2.1 ± 0.2 |

On the other hand, isoproterenol and dcAMP stimulated lipolysis most dramatically in HSL+/+ adipocytes. Moreover, dcAMP, a stable analogue of cAMP, stimulates lipolysis only in HSL+/+ adipocytes. Thus, the cAMP-mediated lipolysis pathway used only HSL as the rate-limiting lipase. These results show that adipomodulin works independently of the cAMP/HSL pathway through a unique mechanism. It is the first molecule described to stimulate lipolysis using a pathway that is independent of cAMP and HSL. Every other lipolytic agent described to date utilizes the cAMP/HSL system.

EXAMPLE 10

Isolation of Adipomodulin Receptor from NIH 3T3-L1 Adipocytes

Working on the hypothesis that adipomodulin is a light chain, we extended these studies to search for a receptor for adipomodulin on NIH 3T3-L1 adipocytes. To this end, we examined the ability of $^{125}$I-Sample-122, a preparation capable of stimulating lipolysis (as discussed above in Examples 1 and 2), to bind to 3T3-L1 adipocytes and compared the results with binding of $^{125}$I-Sample-A (an $^{125}$I-labeled 25-30 kDa preparation from myeloma Patient A, discussed above in Example 7), a preparation incapable of stimulating lipolysis. A commercially available mixture of lambda- and kappa-light chain (Calbiochem, San Diego), incapable of stimulating lipolysis (as discussed above), was used to block non-specific binding sites. The assay was performed at 4° C. to inhibit any cellular metabolism. Radioactive samples to be tested for specific binding were added to cells incubated with an excess of unlabeled competitor (in this case light chain mix) for 2 hours. After extensive washing, the cells were solubilized, and the cell sample counted in a gamma counter. The radioactive counts in the sample represent the molecules bound to the cells (see Kotenko, S. V., Izotova, L. S., Mirochnitchenko, 0. V., Esterova, E., Dickensheets, H., Donnelly, R. P., & Pestka, S., "Identification, cloning, and characterization of a novel soluble receptor that binds IL-22 and neutralizes its activity," J. Immunol., June 15,166(12):7096-103 (2001); Xiao, Q., Jeng, W., & Wheeler, M. B., "Characterization of glucagon-like peptide-1 receptor-binding determinants," J. Mol. Endocrinol., December, 25(3):321-35) (2000). The results of this study are summarized below in Table 6.

TABLE 6

| Ligand | Competitor | Binding, CPM/well |
|---|---|---|
| $^{125}$I-k + λ light chain | λ- + k-light chain | 1335 |
|  |  | 1020 |
| $^{125}$I-Sample-A | λ- + k-light chain | 820 |
|  |  | 1025 |
| $^{125}$I-Sample 122 | λ- + k-light chain | 3230 |
|  |  | 3840 |

The results clearly demonstrate the specific binding of adipomodulin ($^{125}$I-Sample 122) to adipocytes. Binding is not a characteristic of generic light chain molecules (e.g., pooled kappa-lambda mix) or isolated light chain molecules incapable of promoting lipolysis. Therefore, although adipomodulin is a light chain, it has a unique sequence (not found in generic light chains) that has specific binding to adipocytes and induces lipolysis.

The embodiments of this invention described above, including the working examples, are merely exemplary. It is contemplated that numerous other configurations may be used, and the materials used may be selected from numerous materials other than those specifically disclosed. In short, it is the applicant's intention that the scope of the patent issuing herefrom will be limited only by the scope of the appended claims.

What is claimed is:

1. A process for isolating an adipomodulin comprising the steps of:
   a. providing a test sample from a human experiencing weight loss associated with a pathological condition;
   b. isolating the proteins in the test sample that:
      i. have a molecular weight of about 25 kDa to about 30 kDa;
      ii. bind to anti-light chain antibody; and
      iii. bind to adipocytes to promote lipolysis; and
      iv. are not proteoglycans.

2. The process of claim 1, wherein the human is experiencing cancer or HIV.

3. The process of claim 1, wherein the human is experiencing chronic inflammation.

4. The process of claim 1, wherein the test sample comprises the human's urine.

5. The process of claim 1, wherein the test sample comprises the human's blood.

* * * * *